(12) United States Patent
Goldman et al.

(10) Patent No.: US 9,907,638 B2
(45) Date of Patent: Mar. 6, 2018

(54) ATRAUMATIC MEDICAL DEVICE ANCHORING AND DELIVERY SYSTEM WITH ENHANCED ANCHORING

(71) Applicants: Ian L. Goldman, Scottsdale, AZ (US); Yani Deros, Phoenix, AZ (US); Craig Ovans, Chandler, AZ (US)

(72) Inventors: Ian L. Goldman, Scottsdale, AZ (US); Yani Deros, Phoenix, AZ (US); Craig Ovans, Chandler, AZ (US)

(73) Assignee: Ian L. Goldman, Scottsdale, AZ (US)

(*) Notice: Subject to any disclaimer, the term of this patent is extended or adjusted under 35 U.S.C. 154(b) by 910 days.

(21) Appl. No.: 14/033,898

(22) Filed: Sep. 23, 2013

(65) Prior Publication Data

US 2014/0155687 A1   Jun. 5, 2014
US 2016/0113752 A9   Apr. 28, 2016

Related U.S. Application Data

(63) Continuation-in-part of application No. 13/853,867, filed on Mar. 29, 2013, now abandoned, which is a continuation-in-part of application No. 12/538,402, filed on Aug. 10, 2009, which is a continuation-in-part of application No. 12/430,824, filed on Apr. 27, 2009, now Pat. No. 8,216,124, application No. 14/033,898, which is a continuation-in-part of application No. 13/864,190, (Continued)

(51) Int. Cl.
*A61F 2/00* (2006.01)
*A61B 17/04* (2006.01)
*A61B 17/06* (2006.01)
*A61B 17/00* (2006.01)

(52) U.S. Cl.
CPC ........ *A61F 2/0063* (2013.01); *A61B 17/0401* (2013.01); *A61B 17/06109* (2013.01); *A61F 2/0045* (2013.01); *A61B 2017/00805* (2013.01); *A61B 2017/0432* (2013.01); *A61B 2017/0433* (2013.01)

(58) Field of Classification Search
CPC .. A61F 2/0063; A61F 2/0045; A61B 17/0401; A61B 17/06109; A61B 2017/0432; A61B 2017/0433; A61B 2017/00805
See application file for complete search history.

(56) References Cited

U.S. PATENT DOCUMENTS 5,501,683 A   3/1996  Trott
5,573,540 A   11/1996 Yoon
(Continued)

FOREIGN PATENT DOCUMENTS

WO   1999053844   10/1999
WO   WO 2013009834 A1 *  1/2013  ......... A61B 17/0401

*Primary Examiner* — Christine H Matthews
*Assistant Examiner* — Kaylee Wilson
(74) *Attorney, Agent, or Firm* — Dickinson Wright PLLC

(57) ABSTRACT

Systems are delineated for treating urinary incontinence (UI). More generally, systems are delineated for providing medical treatment, wherein such systems include means for attaching a structure to a patient and removing the structure without damage to the structure or the patient. An exemplary system for providing medical treatment comprises a structure for attachment to a patient utilizing at least one retractable barb.

43 Claims, 33 Drawing Sheets

Related U.S. Application Data filed on Apr. 16, 2013, now abandoned, which is a continuation-in-part of application No. 12/538,402, filed on Aug. 10, 2009, which is a continuation-in-part of application No. 12/430,824, filed on Apr. 27, 2009, now Pat. No. 8,216,124.

(60) Provisional application No. 61/618,339, filed on Mar. 30, 2012, provisional application No. 61/095,231, filed on Nov. 3, 2008, provisional application No. 61/624,525, filed on Apr. 16, 2012.

(56) References Cited

U.S. PATENT DOCUMENTS

| | | | |
|---|---|---|---|
| 5,649,963 A | 7/1997 | McDevitt | |
| 6,183,474 B1 | 2/2001 | Bramlet et al. | |
| 6,328,758 B1 | 12/2001 | Tornier et al. | |
| 6,506,190 B1 | 1/2003 | Walshe | |
| 6,652,450 B2 | 11/2003 | Neisz | |
| 6,908,473 B2 | 6/2005 | Skiba et al. | |
| 6,932,834 B2 | 8/2005 | Lizardi et al. | |
| 8,092,366 B2 | 1/2012 | Evans | |
| 8,216,124 B2 | 7/2012 | Goldman | |
| 9,125,717 B2 | 9/2015 | Alexander | |
| 2002/0107430 A1 | 8/2002 | Neisz | |
| 2003/0023137 A1 | 1/2003 | Gellman | |
| 2004/0002735 A1 | 1/2004 | Lizardi et al. | |
| 2004/0172063 A1 | 9/2004 | Li et al. | |
| 2007/0021642 A1 | 1/2007 | Lamoureux et al. | |
| 2007/0021649 A1 | 1/2007 | Nowlin et al. | |
| 2007/0038018 A1 | 2/2007 | Chu | |
| 2008/0009665 A1* | 1/2008 | Merade | A61B 17/06109 600/30 |
| 2008/0023012 A1* | 1/2008 | Dineen | A61B 17/0401 128/848 |
| 2008/0035180 A1 | 2/2008 | Woodson et al. | |
| 2008/0058584 A1 | 3/2008 | Hirotsuka et al. | |
| 2008/0294204 A1* | 11/2008 | Chirico | A61F 2/0805 606/327 |
| 2009/0221868 A1 | 9/2009 | Evans | |
| 2009/0287229 A1* | 11/2009 | Ogdahl | A61B 17/0401 606/151 |
| 2010/0113866 A1 | 5/2010 | Goldman | |
| 2010/0113868 A1 | 5/2010 | Goldman | |
| 2010/0191045 A1* | 7/2010 | Gobron | A61B 17/0401 600/37 |
| 2010/0256442 A1 | 10/2010 | Ogdahl et al. | |
| 2010/0292715 A1 | 11/2010 | Nering et al. | |
| 2011/0288368 A1* | 11/2011 | VanDeWeghe | A61B 17/06109 600/30 |
| 2012/0215058 A1 | 8/2012 | Alexander | |
| 2013/0060078 A1* | 3/2013 | Intoccia, Jr. | A61F 2/0045 600/30 |

\* cited by examiner

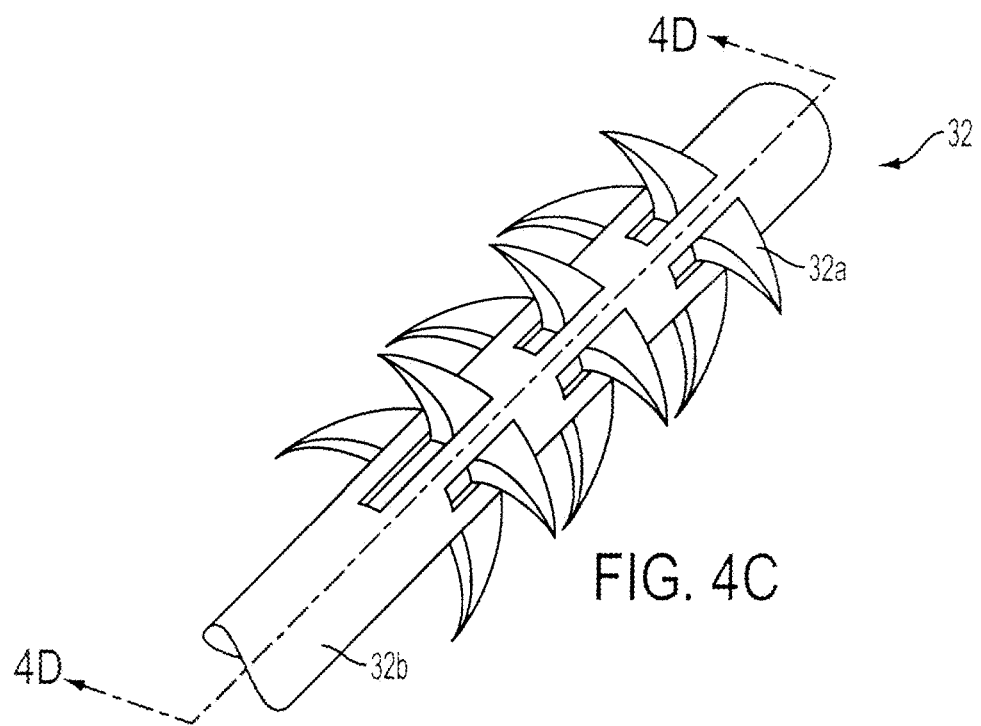

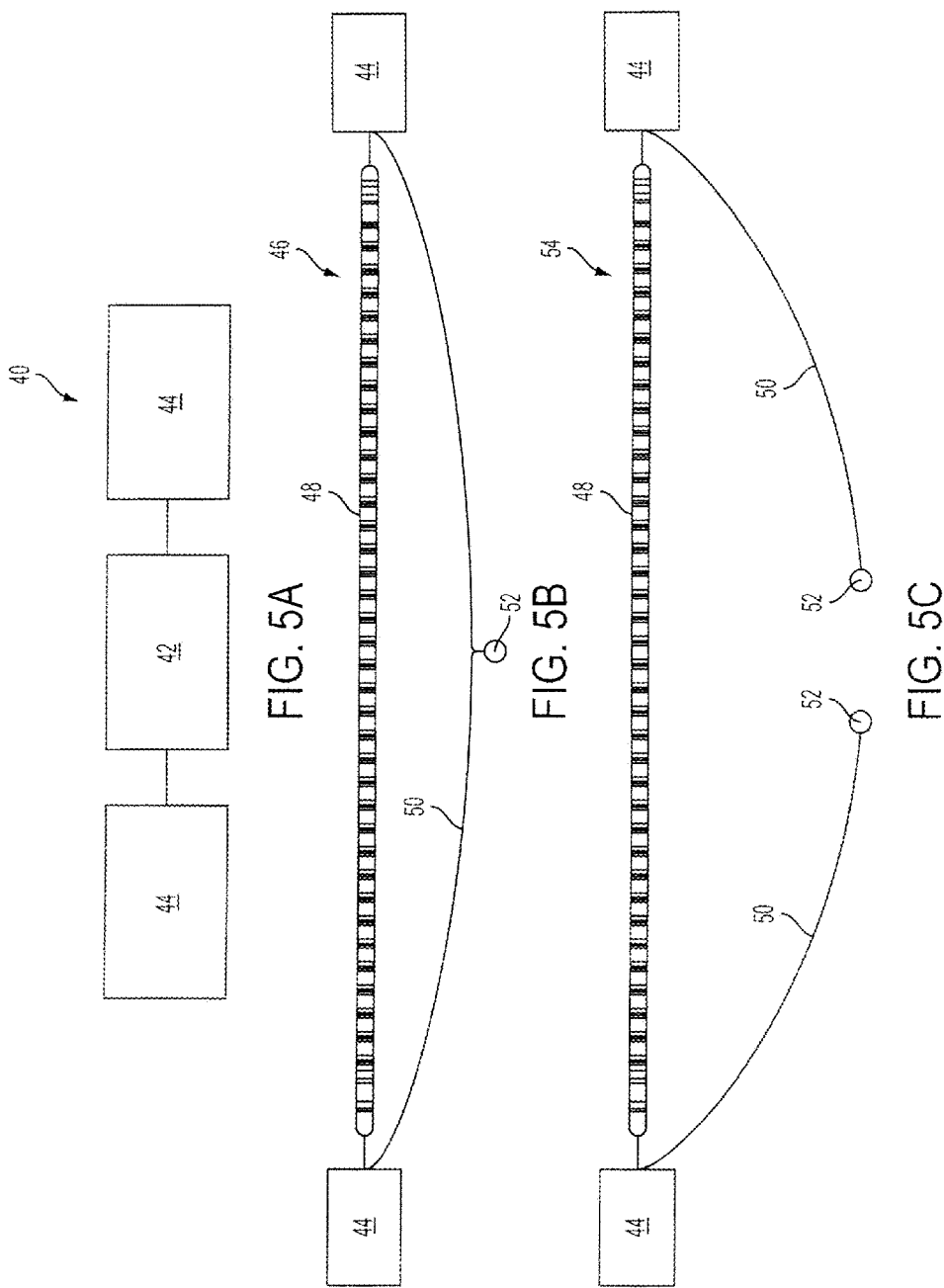

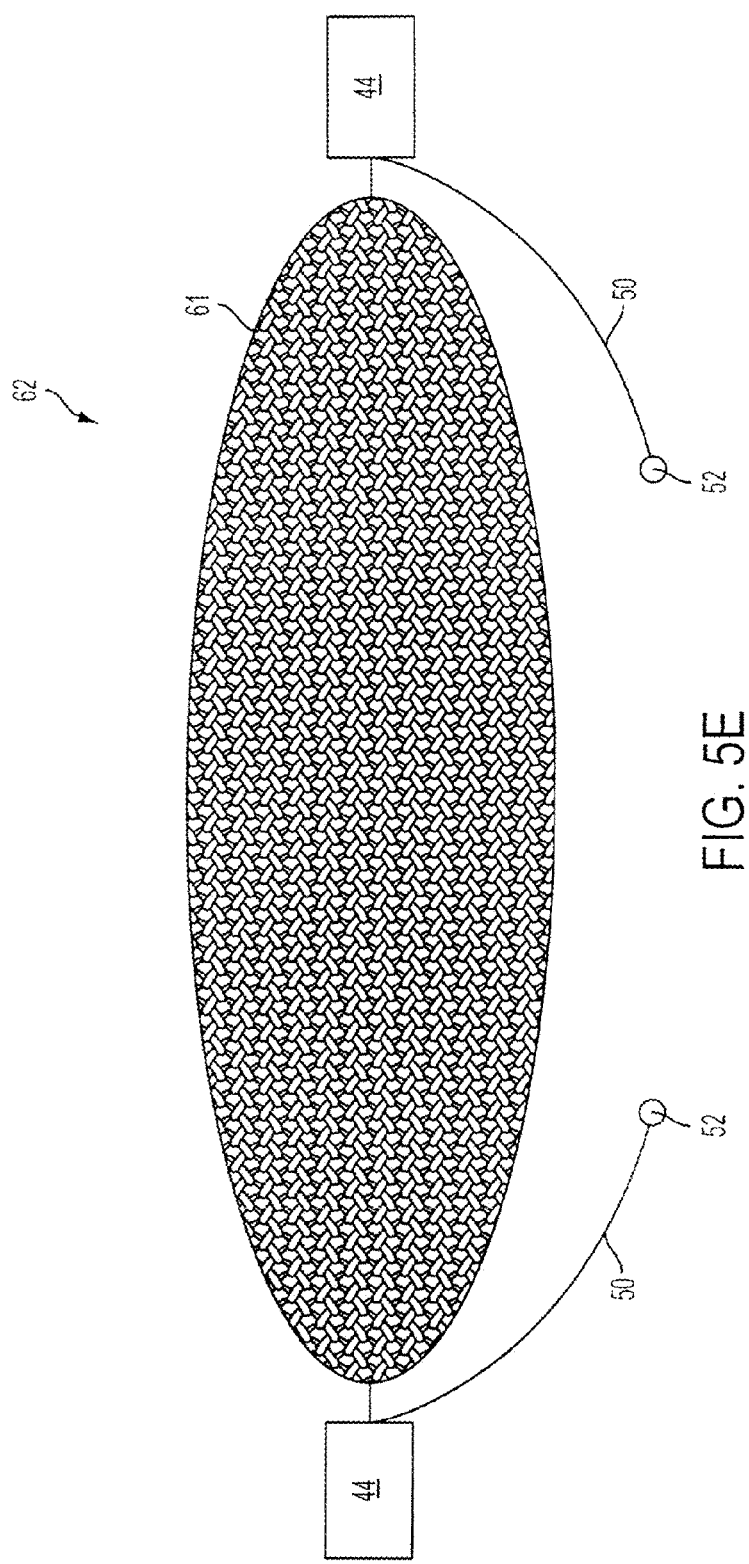

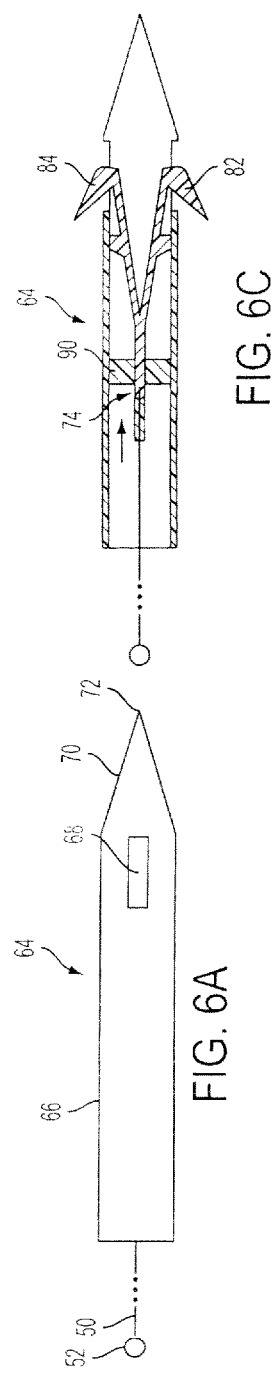
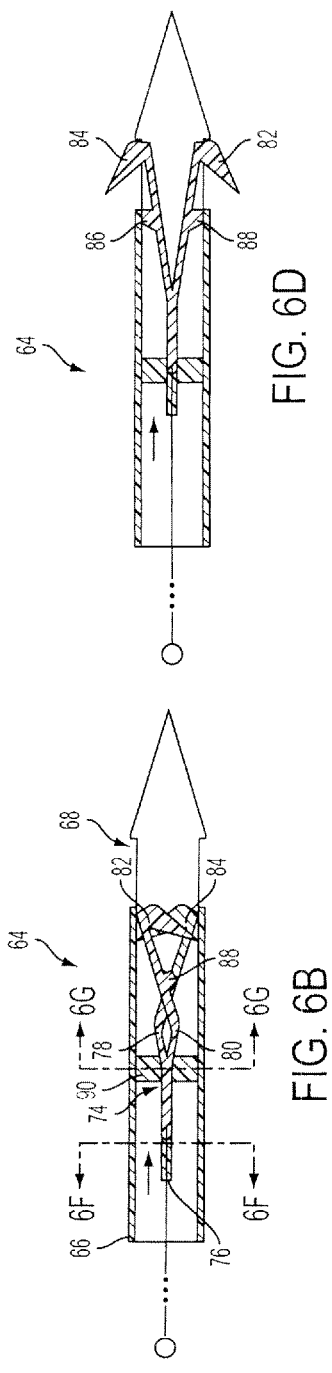
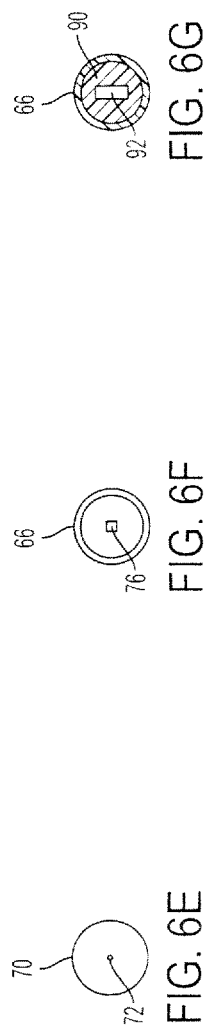

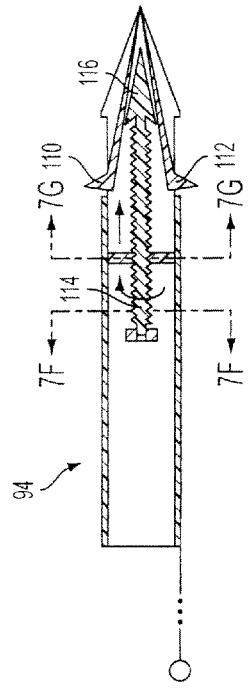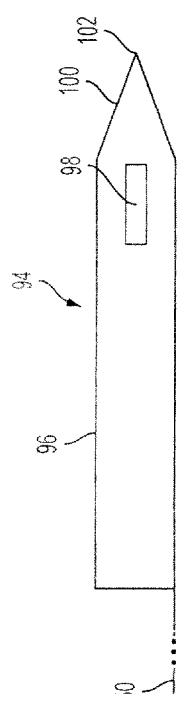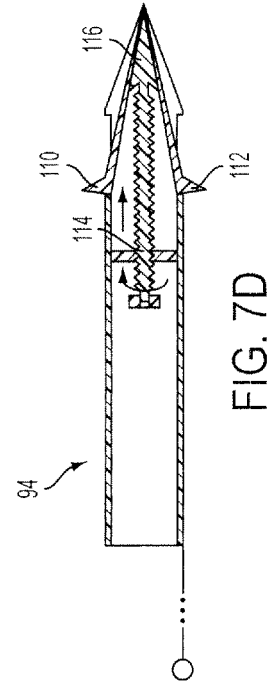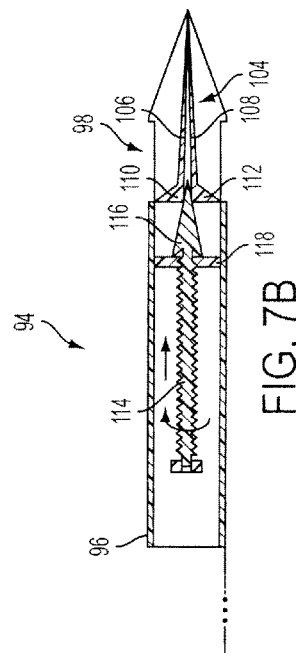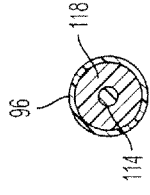

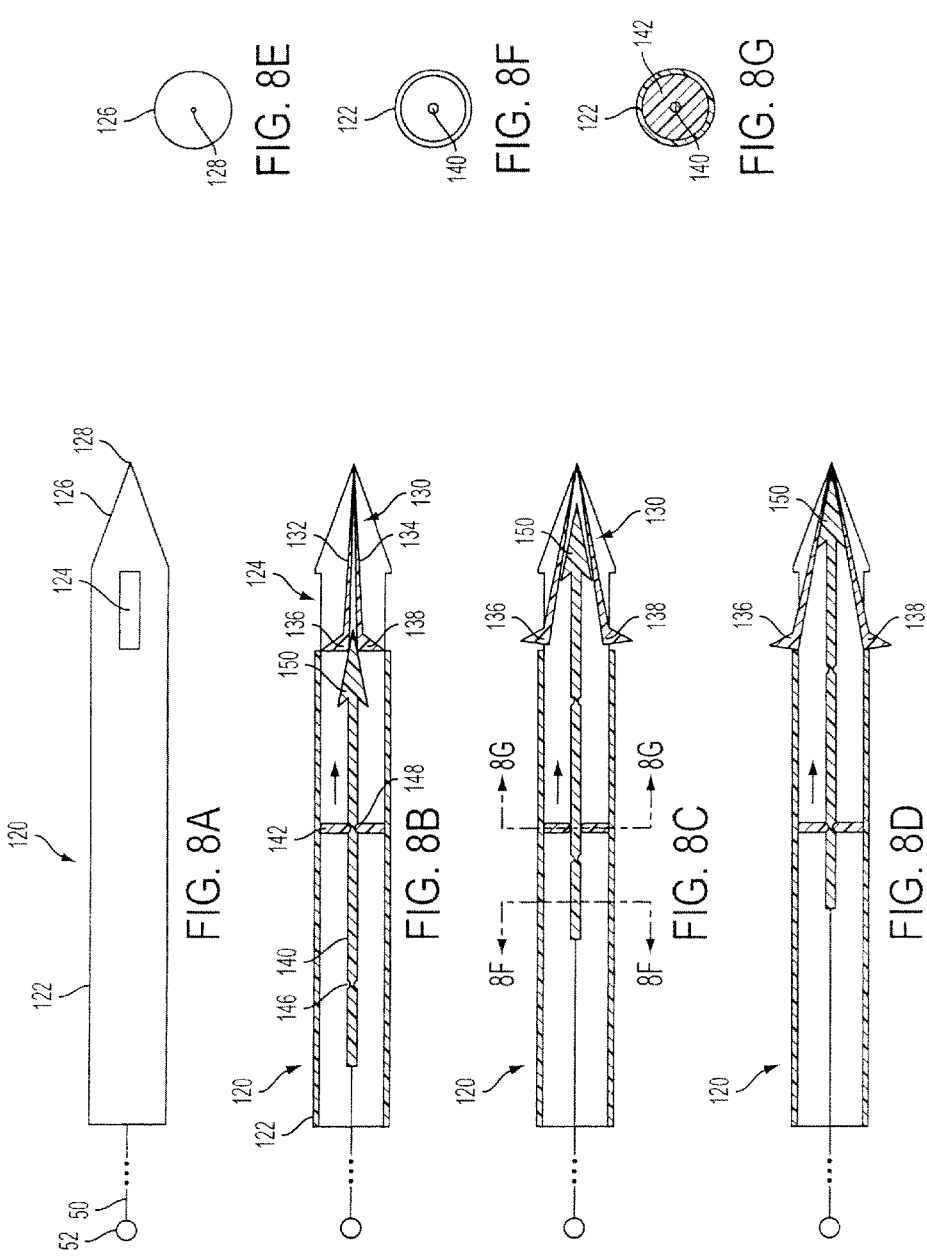

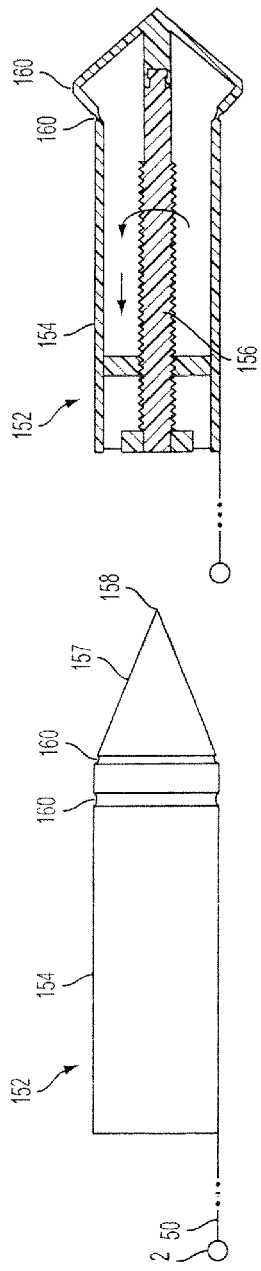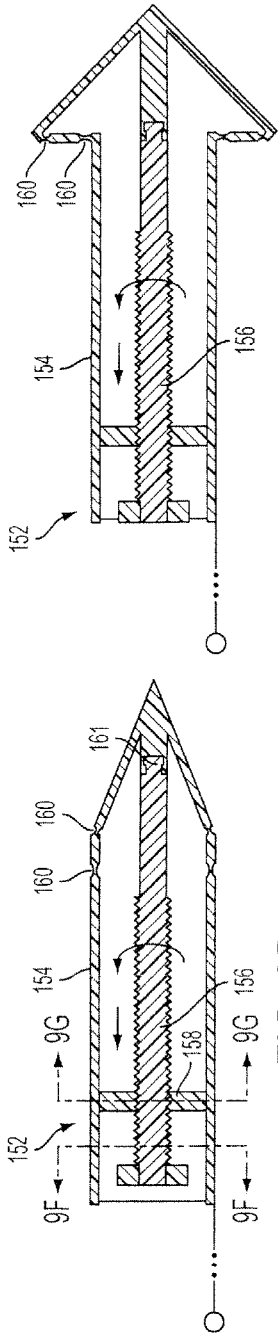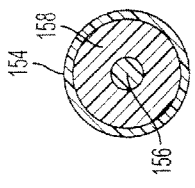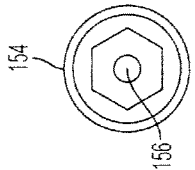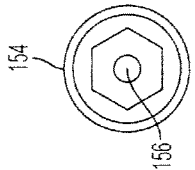

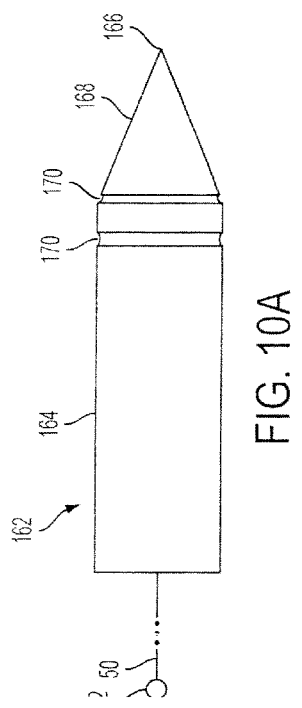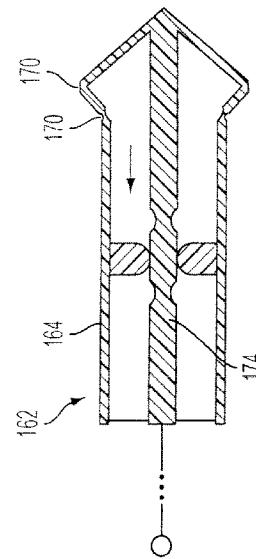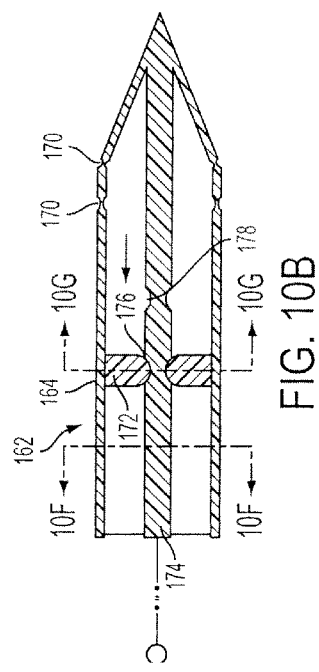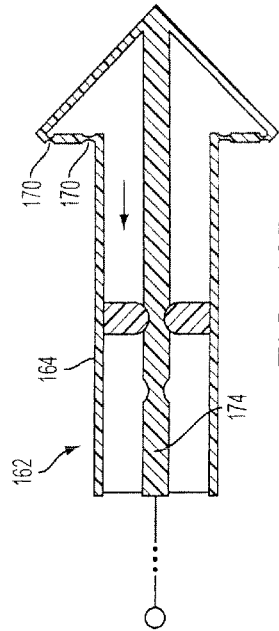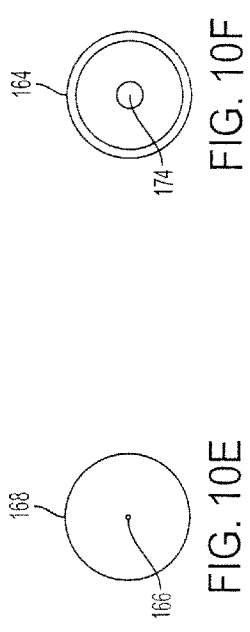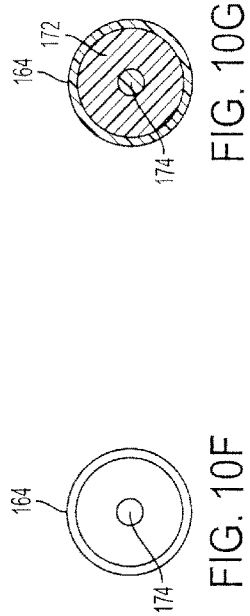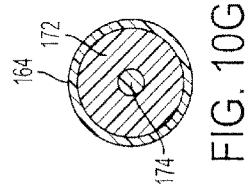

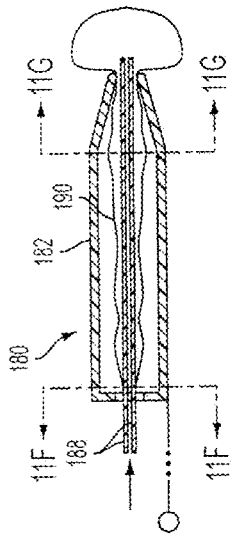
FIG. 11A
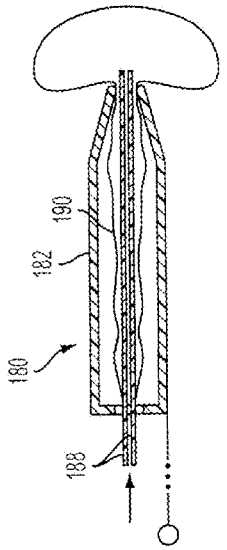
FIG. 11B
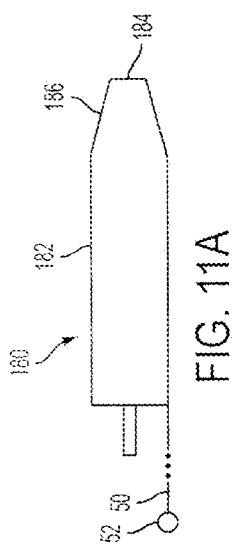
FIG. 11C
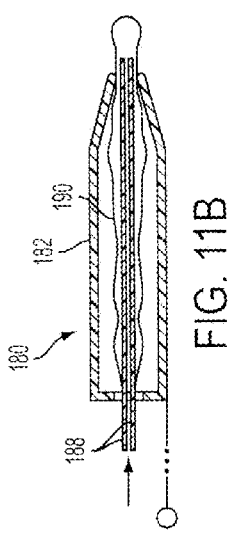
FIG. 11D
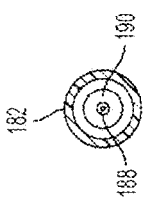
FIG. 11E
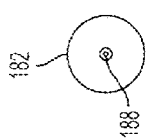
FIG. 11F
FIG. 11G

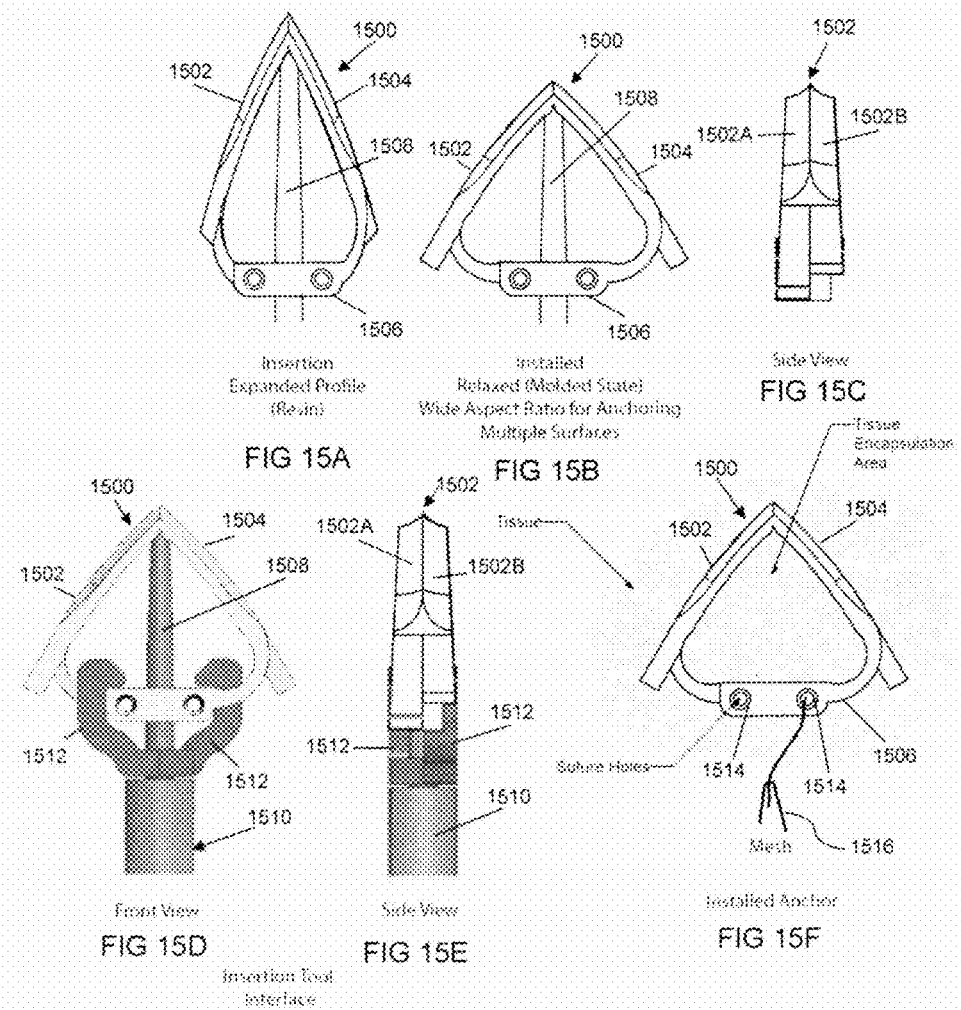

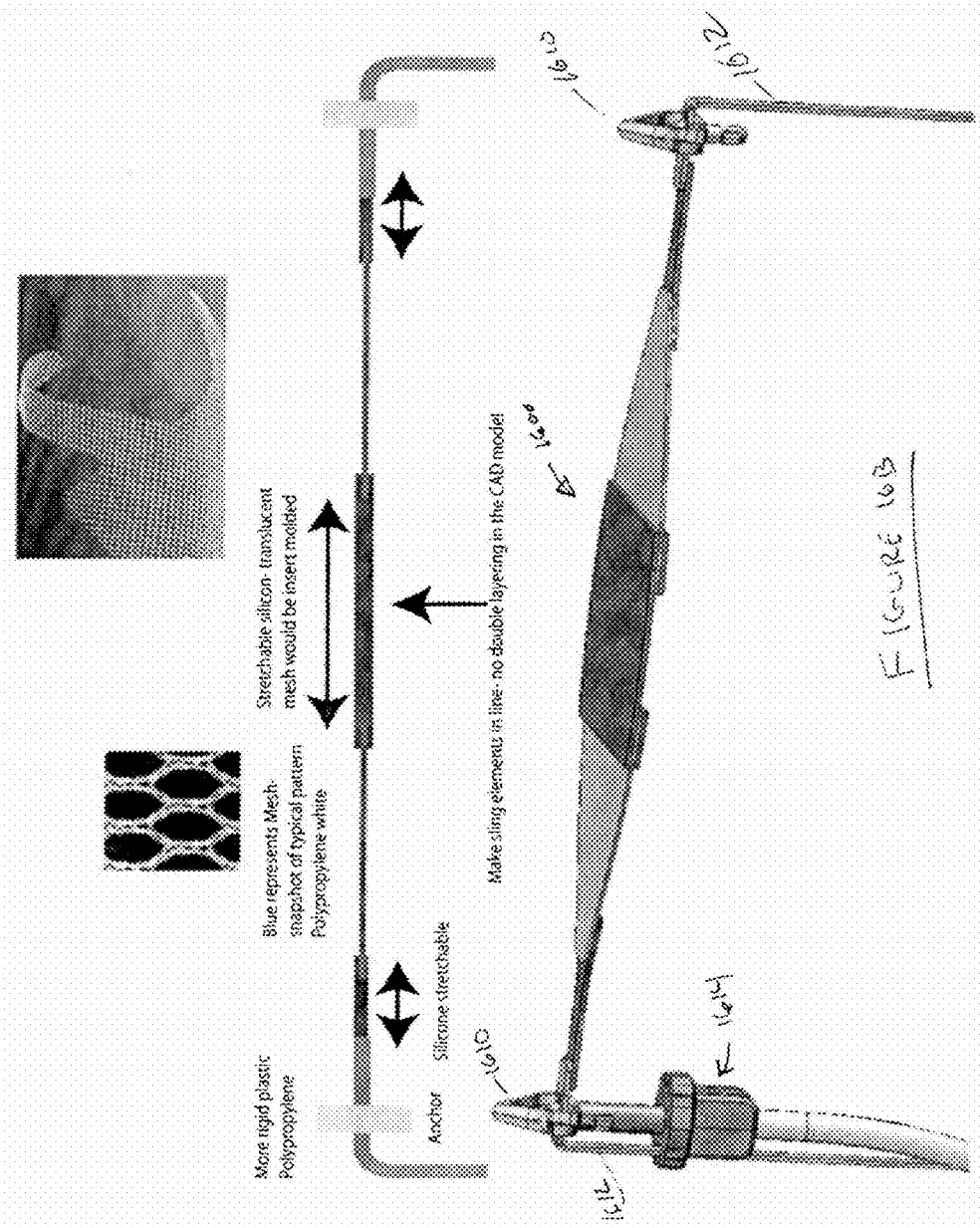

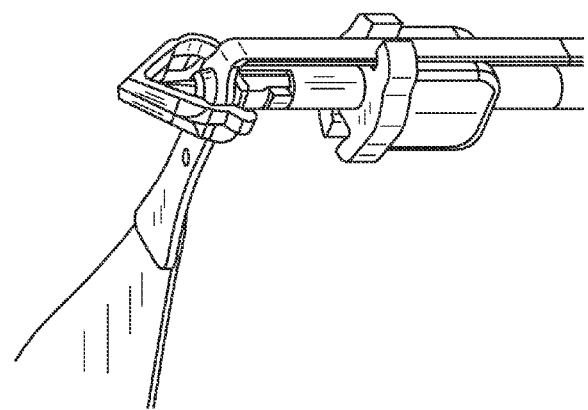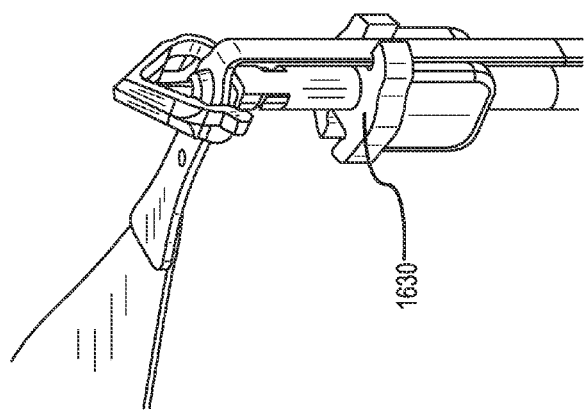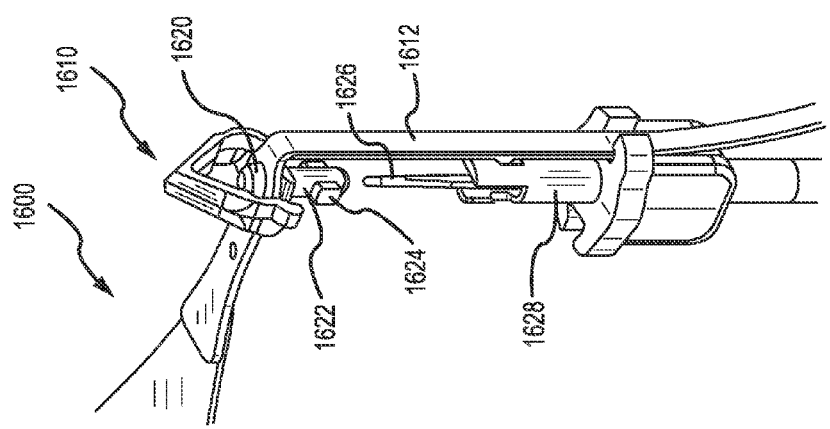
FIGURE 17B

ATRAUMATIC MEDICAL DEVICE ANCHORING AND DELIVERY SYSTEM WITH ENHANCED ANCHORING

CROSS-REFERENCE TO RELATED APPLICATION

This application is a continuation-in-part of and claims priority to: (1) U.S. application Ser. No. 13/853,867, filed Mar. 29, 2013, which is related and claims priority to (A) U.S. Provisional Patent Application No. 61/618,339, filed Mar. 30, 2012 and (B) U.S. patent application Ser. No. 12/538,402, filed Aug. 10, 2009, which is a continuation-in-part of U.S. patent application Ser. No. 12/430,824, filed Apr. 27, 2009 (now U.S. Pat. No. 8,216,124), which claims priority to U.S. Provisional Patent Application No. 61/095,231, filed Nov. 3, 2008 and (2) U.S. application Ser. No. 13/864,190 filed Apr. 16, 2013, which is related and claims priority to (A) U.S. Provisional Patent Application No. 61/624,525, filed Apr. 16, 2012 and (B) U.S. patent application Ser. No. 12/538,402, filed Aug. 10, 2009, which is a continuation-in-part of U.S. patent application Ser. No. 12/430,824, filed Apr. 27, 2009 (now U.S. Pat. No. 8,216,124), which claims priority to U.S. Provisional Patent Application No. 61/095,231, filed Nov. 3, 2008, the disclosures of each of the foregoing applications hereby being incorporated by reference in their entirety.

BACKGROUND OF THE INVENTION

Field of the Invention

The present invention relates to systems and methods for providing medical treatment and, more particularly, to systems and methods for providing medical treatment including means for attaching a structure to a patient and removing the structure without damage, either to the structure or the patient.

Description of the Related Art

Urinary incontinence (UI) is any involuntary leakage of urine. It is a common and distressing problem that may have a profound impact on quality of life. UI often results from an underlying treatable medical condition.

Continence and urination involve a balance between urethral closure and detrusor muscle activity. Urethral pressure normally exceeds bladder pressure, resulting in urine remaining in the bladder. The proximal urethra and the bladder are both within the pelvis. Intra-abdominal pressure increases, e.g., from coughing and sneezing, are typically transmitted to both the urethra and the bladder equally, leaving the pressure differential unchanged, resulting in continence. Normal urination is the result of changes in both of these pressure factors, i.e., urethral pressure decreasing and bladder pressure increasing.

UI affects women of all ages, however, UI is highly prevalent in women across their adult life span and its severity increases linearly with age. Up to 35% of the total population over the age of 60 years is estimated to have UI, with women twice as likely as men to experience UI. One in three women over the age of 60 years is estimated to have UI.

A leading form of UI is known as stress urinary incontinence (SUI). SUI is essentially due to pelvic floor muscle weakness. It results in a loss of small amounts of urine with coughing, laughing, sneezing, exercising or other movements that increase intra-abdominal pressure and thus increase pressure on the bladder. Physical changes resulting from pregnancy, childbirth and menopause often cause SUI.

The urethra is supported by fascia of the pelvic floor. If the fascial support is weakened, as it can be from pregnancy, childbirth or normal physiological changes in the body over the course life, the urethra can move downward at times of increased abdominal pressure, resulting in SUI.

A surgical procedure for treating SUI employs what is commonly referred to as a sling. A sling may consist of any desired material in any desired shape but often consists of a synthetic mesh material or a mesh of biomaterial, e.g., bovine, porcine or the patients' own tissue, in the shape of a ribbon that is placed under the urethra. In practice, a sling surgically implanted beneath a patient's urethra replaces the deficient pelvic floor muscles and provides structural support under the urethra that is sufficient to limit or eliminate SUI.

A common surgical procedure for implanting a sling is referred to as the transobturator procedure. With this procedure, a pair of incisions is made near the groin at the level of the obturator fossa of the pelvic bone and one in the vagina. Sling carriers are passed through from the groin incisions to the vaginal incision. Extension arms connected to the sling are fixedly attached to the sling carriers and the sling carriers are moved to withdraw the extension arms from the pair of incisions made near the groin and to position the sling under the urethra. Thereafter, the extension arms are cut to free the sling carriers, sling tension is adjusted and the incision is closed.

The transobturator procedure involves passing the sling carriers from the two incisions made near the groin at the obturator of the pelvic bone to the vaginal incision. By necessity then, the sling carriers pass through the patient, increasing patient trauma that may include nerve damage. To limit such patient trauma, a less invasive surgical procedure has emerged in which a sling is implanted but only a single vaginal incision is required. However, existing slings, whether implanted using only a vaginal incision or the multiple-incision transobturator procedure, have further limitations, including the inability to reposition the sling.

For example, some current slings include an anchoring mechanism, such as a barbed fastener located at each end of the sling for implanting into the patient's tissue. The anchoring mechanism provides holding strength for the sling until post-surgical tissue growth enables the patient's tissue to provide supplemental long-term holding strength for the sling. It is not uncommon for a surgeon to improperly implant the sling, i.e., when device placement is not optimum for treatment of SUI. At such times, the surgeon must completely remove the sling from the patient and attempt to properly implant the removed sling.

To remove an improperly placed sling, a surgeon typically uses his or her hand, a surgical tool, e.g. a hemostat, or some combination thereof to grasp a portion of the sling and remove it from the patient. The process for removing the sling, once implanted in the patient, is difficult because it is not easy for the surgeon to see and grasp the implanted sling. Moreover, assuming the surgeon can even see or locate an improperly implanted sling, the surgeon must grasp whatever portion of the sling that he or she can to remove the device. Typically, the surgeon grasps an improperly implanted sling at a single position somewhere on the sling and employs considerable force to remove the device. The process of removing an improperly implanted sling using such considerable retraction force applied to a single position on the sling often damages the device. Specifically, the sling is often stretched or torn such that it cannot be reused.

In such instances, the surgeon must use another sling to complete the procedure, resulting in increased cost for the procedure.

Even for slings that do not include an anchoring mechanism, such as a barbed fastener located at each end of the sling, device removal is an issue for an improperly implanted sling. In such instances, following device implantation with the transobturator procedure, the sling carriers which are fixed to the sling extension arms cannot be backed out to remove the sling from beneath the urethra. Accordingly, it is not possible to remove the sling for repositioning, if desired.

Existing slings also have limited holding strength. As noted above, post-surgical tissue growth enables the patient's tissue to provide supplemental long-term holding strength for the sling. However, until such time that post-surgical tissue growth enables the patient's tissue to provide supplemental long-term holding strength for the sling, means for providing preliminary holding strength are employed. Such preliminary holding strength systems include those which employ an anchoring mechanism, such as a barbed fastener located at each end of the sling, for implanting into the patient's tissue. Other slings do not employ an anchoring mechanism and simply rely on a friction fit between the sling and the patient's tissue to hold the sling in place. Regardless of the type of preliminary holding strength system that is employed, current slings continue to move following surgery, and therefore, would benefit from improved holding strength.

A need exists for systems and methods for treatment of SUI, which overcome these and other problems associated with the prior art. And more generally, a need exists for systems and methods for providing medical treatment including means for attaching a structure to a patient and removing the structure without damage, either to the structure or the patient.

SUMMARY OF THE INVENTION

In accordance with an embodiment of the present invention, a system is disclosed for providing medical treatment to a patient. The system comprises a structure for attachment to the patient, the structure having a first end and a second, opposing end; a first aperture located near the first end of the structure, the first aperture including a first key for accepting the insertion of a first retractable barb and for establishing a desired alignment of the structure with respect to the first retractable barb; and a second aperture located near the second end of the structure, the second aperture including a second key for accepting the insertion of a second retractable barb and for establishing a desired alignment of the structure with respect to the second retractable barb.

The system further includes the first retractable barb and the second retractable barb, wherein each retractable barb comprises a pair of movable arms, each having a first and a second end, the first ends of the pair of movable arms being coupled together; a base member having a first end and a second end, each end of which is coupled in proximity to a second end of a respective one of the pair of movable arms; and wherein the pair of movable arms and the base member form a triangular structure having an outer surface and an inner surface, the inner surface forming an aperture between the pair of movable arms and the base member for tissue growth.

In accordance with another embodiment of the present invention, a system is disclosed for providing medical treatment to a patient, the system comprising a structure for attachment to the patient, the structure having a generally rectangular shape and having extending therefrom a plurality of arms, each arm including a proximal end coupled to the generally rectangular shape of the structure and a distal end; an aperture located near the distal end of each arm, each aperture including a key for accepting the insertion of a retractable barb and for establishing a desired alignment of the structure with respect to the retractable barb; and a plurality of apertures located near a perimeter portion of the generally rectangular shape of the structure, each aperture of the plurality of apertures including a key for accepting the insertion of a retractable barb and for establishing a desired alignment of the structure with respect to the retractable barb.

The system further includes a retractable barb coupled to each aperture in the structure, wherein each retractable barb comprises a pair of movable arms, each having a first and a second end, the first ends of the pair of movable arms being coupled together; a base member having a first end and a second end, each end of which is coupled in proximity to a second end of a respective one of the pair of movable arms; and wherein the pair of movable arms and the base member form a triangular structure having an outer surface and an inner surface, the inner surface forming an aperture between the pair of movable arms and the base member for tissue growth.

In accordance with yet another embodiment of the present invention, a retractable barb is disclosed for attaching a portion of a medical device to a patient, the retractable barb comprising a pair of movable arms, each having a first and a second end, the first ends of the pair of movable arms being coupled together; a base member having a first end and a second end, each end of which is coupled in proximity to a second end of a respective one of the pair of movable arms; and wherein the pair of movable arms and the base member form a triangular structure having an outer surface and an inner surface, the inner surface forming an aperture between the pair of movable arms and the base member for tissue growth.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

FIGS. 1A and 1B together show part of a sequence for assembly of the medical device.

FIGS. 1D and 1E together show part of a sequence for assembly of the medical device.

FIG. 4C is a partial perspective view of another embodiment of a fastener for use with any embodiment of a medical device for use in treatment of UI, in accordance with systems and methods consistent with the present invention.

FIGS. 4F-4H show exemplary tools for inserting and/or extracting a fastener.

FIG. 5A is a block diagram of an embodiment of a system for providing medical treatment, in accordance with systems and methods consistent with the present invention.

FIG. 5B is a side elevation view of an embodiment of a system for providing medical treatment, in accordance with systems and methods consistent with the present invention.

FIG. 5C is a side elevation view of another embodiment of a system for providing medical treatment, in accordance with systems and methods consistent with the present invention.

FIG. 5E is a plan view of another embodiment of a system for providing medical treatment, in accordance with systems and methods consistent with the present invention.

FIG. 6A is a side elevation view of an embodiment of a fastener for use in a system for providing medical treatment, in accordance with systems and methods consistent with the present invention.

FIGS. 6B-6D are a sequence of side elevation views of the embodiment of a fastener from FIG. 6A. Each side elevation view includes a cross-section to show interior portions as retractable barbs transition from a stowed state in FIG. 6B to a deployed state in FIG. 6D.

FIG. 6E is a side elevation view of the embodiment of a fastener from FIG. 6A, taken from the perspective of looking into the front tip of the fastener.

FIGS. 6F and 6G are cross-sectional views taken respectively along lines 6F-6F and 6G-6G.

FIG. 7A is a side elevation view of another embodiment of a fastener for use in a system for providing medical treatment, in accordance with systems and methods consistent with the present invention.

FIGS. 7B-7D are a sequence of side elevation views of the embodiment of a fastener from FIG. 7A. Each side elevation view includes a cross-section to show interior portions as retractable barbs transition from a stowed state in FIG. 7B to a deployed state in FIG. 7D.

FIG. 7E is a side elevation view of the embodiment of a fastener from FIG. 7A, taken from the perspective of looking into the front tip of the fastener.

FIGS. 7F and 7G are cross-sectional views taken respectively along lines 7F-7F and 7G-7G.

FIG. 8A is a side elevation view of another embodiment of a fastener for use in a system for providing medical treatment, in accordance with systems and methods consistent with the present invention.

FIGS. 8B-8D are a sequence of side elevation views of the embodiment of a fastener from FIG. 8A. Each side elevation view includes a cross-section to show interior portions as retractable barbs transition from a stowed state in FIG. 8B to a deployed state in FIG. 8D.

FIG. 8E is a side elevation view of the embodiment of a fastener from FIG. 8A, taken from the perspective of looking into the front tip of the fastener.

FIGS. 8F and 8G are cross-sectional views taken respectively along lines 8F-8F and 8G-8G.

FIG. 9A is a side elevation view of another embodiment of a fastener for use in a system for providing medical treatment, in accordance with systems and methods consistent with the present invention.

FIGS. 9B-9D are a sequence of side elevation views of the embodiment of a fastener from FIG. 9A. Each side elevation view includes a cross-section to show interior portions as a retractable barb transitions from an initial state in FIG. 9B to a deployed state in FIG. 9D.

FIG. 9E is a side elevation view of the embodiment of a fastener from FIG. 9A, taken from the perspective of looking into the front tip of the fastener.

FIGS. 9F and 9G are cross-sectional views taken respectively along lines 9F-9F and 9G-9G.

FIG. 10A is a side elevation view of another embodiment of a fastener for use in a system for providing medical treatment, in accordance with systems and methods consistent with the present invention.

FIGS. 10B-10D are a sequence of side elevation views of the embodiment of a fastener from FIG. 10A. Each side elevation view includes a cross-section to show interior portions as a retractable barb transitions from an initial state in FIG. 10B to a deployed state in FIG. 10D.

FIG. 10E is a side elevation view of the embodiment of a fastener from FIG. 10A, taken from the perspective of looking into the front tip of the fastener.

FIGS. 10F and 10G are cross-sectional views taken respectively along lines 10E-10F and 10G-10G.

FIG. 11A is a side elevation view of another embodiment of a fastener for use in a system for providing medical treatment, in accordance with systems and methods consistent with the present invention.

FIGS. 11B-11D are a sequence of side elevation views of the embodiment of a fastener from FIG. 11A. Each side elevation view includes a cross-section to show interior portions as a retractable barb transitions from an initial state in FIG. 11B to a deployed state in FIG. 11D.

FIG. 11E is a side elevation view of the embodiment of a fastener from FIG. 11A, taken from the perspective of looking into the front tip of the fastener.

FIGS. 11F and 11G are cross-sectional views taken respectively along lines 11F-11F and 11G-11G.

FIGS. 15A-15F show an embodiment of a retractable barb with enhanced anchoring, in accordance with systems and methods consistent with the present invention.

FIGS. 16A-16B show an embodiment of an improved sling including a tool for employing same, as depicted in FIG. 16B, in accordance with systems and methods consistent with the present invention.

FIGS. 17A-17B show an embodiment of an improved anchoring mechanism, including a tool for employing same, as depicted in FIG. 17B, in accordance with systems and methods consistent with the present invention.

DESCRIPTION OF THE EMBODIMENTS

Reference will now be made in detail to the present exemplary embodiments of the invention, examples of which are illustrated in the accompanying drawings.

Figure 1A:
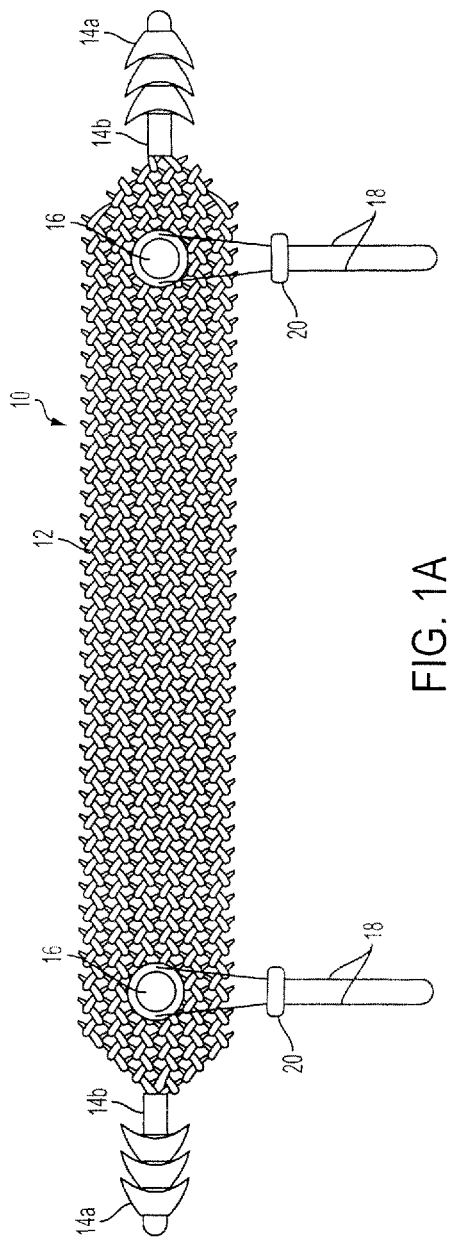
FIG. 1A is a plan view of an embodiment of a medical device for use in treatment of urinary incontinence (UI), in accordance with systems and methods consistent with the present invention.

Referring to FIG. 1A, a plan view is shown of an embodiment of a medical device (or system) 10 for use in treatment of urinary incontinence (UI), in accordance with systems and methods consistent with the present invention. Medical device 10 comprises what those skilled in the art would refer to as an enhanced sling for treatment of UI. Those skilled in the art also recognize that a sling, such as medical device 10, may be successful for treating stress urinary incontinence (SUI) and any other type of UI, now known or later discovered.

Moreover, those skilled in the art understand that a sling, such as medical device 10, may be surgically implanted using a well known and minimally invasive procedure employing the insertion of a sling into a single vaginal incision. This procedure involves inserting a sling, such as medical device 10, into the vaginal incision, positioning the sling under the patient's urethra and anchoring the ends of the sling into the patient's tissue to provide support to the urethra. When such urethral support is applied at the correct position, a sling, such as medical device 10, can successfully ameliorate UI. As the details of this surgical procedure are well known, further details of the procedure are deemed unnecessary to understand the present invention and are therefore not set forth here.

Still with reference to FIG. 1A, medical device 10 may include a strip 12, one or more fasteners 14 (collectively, elements 14a and 14b), one or more apertures 16, one or more aperture covers 20 and one or more cords 18.

Strip 12 may comprise any material now known or later discovered for making slings that may be employed to treat UI. For example, strip 12 may comprise a synthetic mesh material, a mesh of biomaterial or a combination thereof. As is the case with current slings, regardless of the material employed to fabricate strip 12, strip 12 requires some degree of flexibility. For example, strip 12 should have enough flexibility to permit the ends of strip 12 to be anchored above the center of strip 12, essentially providing a curved, hammock-like structure to support a portion of the patient's urethra. At the same time, however, strip 12 should also provide rigidity suitable to support the patient's urethra. In general, strip 12 may have rigidity and flexibility consistent with now known or later discovered slings that may be employed to treat UI.

Strip 12 may have any desired shape and dimensions, however, in an exemplary embodiment, strip 12 may have a length in the range of 7 cm to 9 cm, a width in the range of 1 cm to 2 cm and a thickness in the range of 0.5 mm to 1 mm. Those skilled in the art understand that the aforementioned dimensions may extend outside the recited ranges for any reason, if so desired. For example, a larger patient may require a strip 12 of longer, wider and/or thicker dimensions. The ends of strip 12 may be tapered, as shown, tapered to a different degree or not tapered at all.

Strip 12 includes a primary axis, which is not labeled in FIG. 1A but extends lengthwise along the center of strip 12. Strip 12 also includes a secondary axis, which is also not labeled but extends widthwise (or vertically in FIG. 1A) and crosses the center of strip 12. Continuing with the hammock analogy set forth above, during surgical implantation, strip 12 is generally placed such that the patient's urethra rests orthogonally with respect to the primary axis. To be clear, this arrangement is not analogous to a person sleeping in a hammock in which case the person rests in alignment with the length of the hammock. The surface of strip 12 that is shown in FIG. 1A is not the urethra resting surface; the opposite side of strip 12, as shown in FIGS. 1C-1E, provides the urethra resting surface.

Still with reference to FIG. 1A, medical device 10 may also include one or more fasteners 14. As shown, medical device 10 may include a pair of fasteners 14, one coupled to each end of strip 12. Fasteners 14 may comprise any structure suitable for anchoring the ends of strip 12 into a patient's tissue, thereby providing support to the patient's urethra with strip 12. Fasteners 14 may also be made from any material suitable for patient implantation and anchoring the ends of strip 12 into patient tissue, such as a plastic, a metal, a composite or any combination thereof suitable for patient implantation.

In an exemplary embodiment, fasteners 14 may include a shaft 14b coupled to an end of strip 12 and one or more barbs 14a coupled to shaft 14b. As shown in FIG. 1A, fasteners 14 include a plurality of barbs 14a, however, a single barb 14a may be employed. Moreover, fasteners 14 are not limited to the structure, as shown in FIG. 1A. Rather, fasteners 14 may employ any structure suitable for anchoring the ends of strip 12 into patient tissue.

Additionally, and as will be discussed in detail below, fasteners 14 may be retractable. More specifically, fasteners 14 may have selectable positions. For example, fasteners 14 may include a first position in which the barb 14a or barbs 14a are extended, as shown in FIG. 1A, for anchoring into patient tissue, and a second position in which the barb 14a or barbs 14a are retracted to minimize tissue trauma when fastener 14 is removed from the patient's tissue. Moreover, it may be desirable to have the barb 14a or barbs 14a retracted during implanting of medical device 10. While an exemplary embodiment for providing a retractable fastener 14 is set forth below in connection with the description of FIGS. 4C-4E, those skilled in the art understand that fasteners 14 may be constructed in any one of a variety of different ways to provide a retractable fastener.

Again with reference to FIG. 1A, medical device 10 may also include one or more apertures 16, one or more aperture covers 20 and one or more cords 18.

The one or more apertures 16 may take any shape or size and may be positioned anywhere along strip 12. In an exemplary embodiment, however, strip 12 may include a pair of apertures 16, each being located closer to a respective end of strip 12 than to the opposing end of strip 12. For example, as shown in FIG. 1A, apertures 16 are located in proximity to the two ends of strip 12. As also shown in FIG. 1A, apertures 16 may be circular in shape and include a diameter larger than the diameter of the smaller spaces between the mesh strands forming strip 12.

As shown in FIGS. 1D and 1E, strip 12 may provide an extension or support shelf 24 within each aperture 16 that provides a seating surface for a corresponding aperture cover 20. Support shelves 24 may also provide locations where the ends of cords 18 may be fixedly attached. For each aperture 16 shown in FIG. 1A, a cord 18 may extend through the apertures in aperture cover 20 and be fixedly attached at both ends to the respective support shelf 24. Cords 18 may be made from any material suitable for patient implantation, such as a plastic, a metal, a composite or any combination thereof suitable for patient implantation.

The one or more apertures 16, one or more aperture covers 20 and one or more cords 18 collectively provide two separate functions for medical device 10. First, they enable the medical practitioner to remove an improperly placed strip 12, without damaging strip 12. For example, as noted for each aperture 16 shown in FIG. 1A, a cord 18 may extend through the apertures in an aperture cover 20 and be fixedly attached at both ends to a respective support shelf 24. Accordingly, if a medical practitioner is dissatisfied with the placement of strip 12, once it is anchored to the patient with fasteners 14, the practitioner may grasp aperture covers 20 (either by hand or with a suitable surgical instrument) and pull back on aperture covers 20 to remove fasteners 14 from patient tissue. Unlike prior art systems, this may be done without damaging strip 12, thereby permitting reuse of the same strip 12. Moreover, in embodiments of medical device 10 with 14 retractable fasteners 14, the barb 14a or barbs 14 may be retracted 14 prior to removal of strip 12 to minimize patient trauma.

A second function of medical device 10 that is collectively provided by the one or more apertures 16, one or more aperture covers 20 and one or more cords 18 is the ability to provide additional holding support for strip 12. For example, assuming that the medical practitioner has anchored strip 12 to a desired position, the practitioner may cut each cord 18 (approximately at its midpoint), slide aperture covers 20 along their respective cords 18 and tie cords 18 snugly against their respective aperture covers 20 such that aperture covers 20 press firmly against respective support shelves 24, creating a force applied against the patient's tissue to help hold medical device 10 in place (hereinafter the "seating force"). Aperture covers 20 may be made from any desired material that is suitable for patient implantation and more rigid than strip 12, such as a plastic, a metal, a composite or any desired combination thereof. This rigidity differential between aperture cover 20 and strip 12 improves the effectiveness of the seating force holding medical device 10 in place.

Additionally, as shown in FIG. 1C, an array of protrusions 22 may extend from strip 12 in proximity to apertures 16. As such, the seating force will be applied near the array of protrusions 22, which should further enhance the effectiveness of the seating force holding medical device 10 in place. The array of protrusions 22 may take any form or shape. As shown in FIGS. 1C-1E, the array of protrusions 22 is circular and arranged in proximity to the perimeter of apertures 16, though the array of protrusions 22 may take any other desired shape and may or may not reside in proximity to the perimeter of apertures 16. The protrusions forming array 22 are in a curved shape bending outwardly with respect to apertures 16. Those skilled in the art understand, however, that any other shape or arrangement may be employed for the protrusions forming array 22, such as inwardly bending protrusions. The protrusions comprising array 22 may comprise any material suitable for patient implantation and for supplementing the holding support for medical device 10 such as a plastic, a metal, a composite or any combination thereof.

In an exemplary embodiment of medical device 10, medical device 10 comprises an integral device in that the strip 12, the one or more fasteners 14, the one or more apertures 16, the one or more aperture covers 20 and the one or more cords 18 are all fabricated into a single device in which no additional parts are required (although there may be tools, which are not part of the medical device 10, that may be employed to insert and/or remove medical device 10). In a variation of medical device 10, medical device 10 may comprise an integral device except for the following distinction, namely, that the cords 18, as shown in FIG. 1A, would be precut, such that each cord 18 would have an end attached to a respective support shelf 24 and an opposite free end. In this instance, the aperture covers 20 would not be held by a closed loop of a cord 18; instead the medical practitioner would thread each cord 18 into the respective apertures in the aperture covers 20 when he was ready to synch down the aperture covers 20 and tie them in place with the cords 18. Thus, in this variation, medical device 10 may be considered an integral device, except for the aperture covers 20, which are separate and installed during the surgical procedure.

Figure 1B:
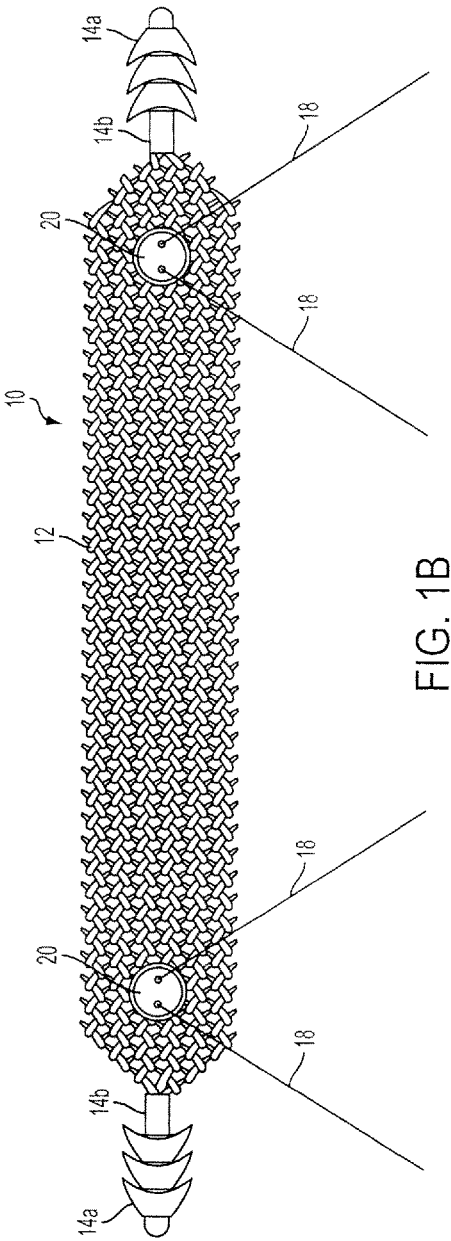
FIG. 1B is a plan view of the embodiment of the medical device shown in FIG. 1A, in accordance with systems and methods consistent with the present invention.
Figure 1C:
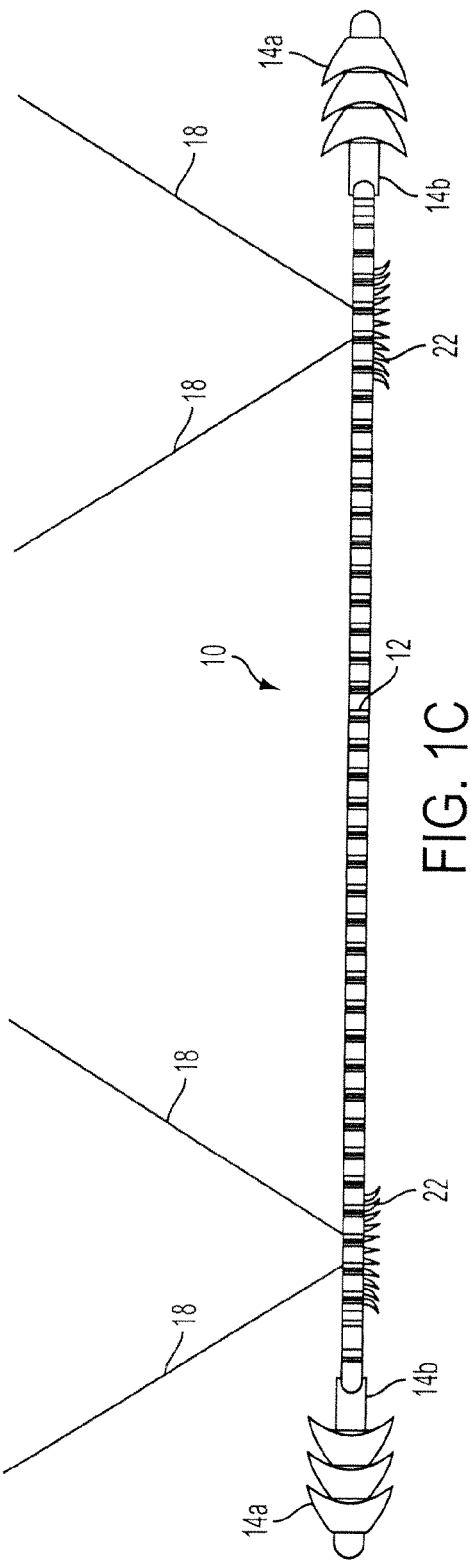
FIG. 1C is a side elevation view of the embodiment of the medical device shown in FIG. 1B, in accordance with systems and methods consistent with the present invention.
Figure 1D:
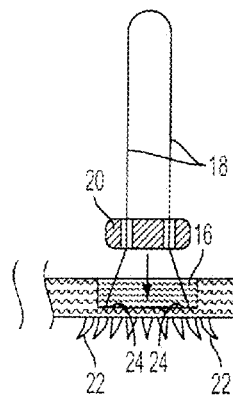
FIGS. 1D and 1E are partial cross-sectional views taken along line D-D of FIG. 1F, in accordance with systems and methods consistent with the present invention.
Figure 1E:
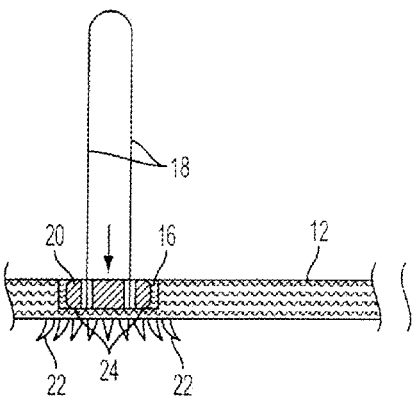

Referring to FIG. 1B, a plan view is shown of the embodiment of medical device 10 shown in FIG. 1A. FIGS. 1A and 1B together show part of a sequence for assembly of medical device 10. In FIG. 1B, we assume that fasteners 14 are anchored in patient tissue and the medical practitioner is satisfied with device placement. Accordingly, the practitioner has cut each cord 18 (assuming the integral embodiment of medical device 10) and slid aperture covers 20 along their respective cords 18 in preparation to tie cords 18 snugly against their respective aperture covers 20, creating the seating force to help hold medical device 10 in place. We note for the sake of clarity, however, that no patient is shown and that the angular positioning of medical device 10 does not reflect what angular positioning would actually look like installed in a patient (e.g., fasteners 14 would be canted up, instead of lying flat, as shown).

Referring to FIG. 1C, a side elevation view is shown of the embodiment of medical device 10 of FIG. 1B. As in FIG. 1B, we assume that fasteners 14 are anchored in patient tissue and the medical practitioner is satisfied with device placement. Accordingly, the practitioner has cut each cord 18 (assuming the integral embodiment of medical device 10) and slid aperture covers 20 along their respective cords 18 in preparation to tie cords 18 snugly against their respective aperture covers 20, creating the seating force to help hold medical device 10 in place. Again, we note for the sake of clarity, however, that no patient is shown and that the angular positioning of medical device 10 does not reflect what angular positioning would actually look like installed in a patient (e.g., fasteners 14 would be canted up, instead of lying flat, as shown).

Referring to FIGS. 1D and 1E, partial cross-sectional views are shown of the embodiment of medical device 10 in FIG. 1B. FIGS. 1D and 1E together show the seating of aperture cover 20 against support shelf 24. In FIG. 1D, the ends of cord 18 are shown fixedly attached to support shelf 24. FIG. 1D also shows that the attachment points for cord 18 are not aligned with the apertures in aperture cover 20, though they could be, if desired, however, having a slight alignment offset improves the holding strength once cord 18 is severed and tied down against aperture cover 20. It also bears mentioning that the space between the outer edge of aperture cover 20 and the wall forming aperture 16 may be exaggerated, i.e., there may be a snug mechanical fit between the outer edge of aperture cover 20 and the wall forming aperture 16.

Alternatively, there may be a small space between the outer edge of aperture cover 20 and the wall forming aperture 16. Additionally, whether there is a space or a snug mechanical fit between the outer edge of aperture cover 20 and the wall forming aperture 16, various additional mechanical interfaces may be employed. For example, a ring or other protrusion (not shown) may extend slightly from the outer edge of aperture cover 20 and a corresponding notch (not shown) may be produced in the wall forming aperture 16, such that the ring or other protrusion mates with the notch to provide a tactile sensation to the medical practitioner when aperture cover 20 is in place (prior to tying cords 18). Similarly, one or more posts or other protrusions (not shown) may extend slightly from the bottom surface of aperture cover 20 for mating with one or more corresponding apertures (not shown), which may be produced in support shelf 24, such that the one or more posts or other protrusions provide a tactile sensation to the medical practitioner when aperture cover 20 is in place, as well as assisting in proper alignment of aperture cover 20.

Figure 1F:
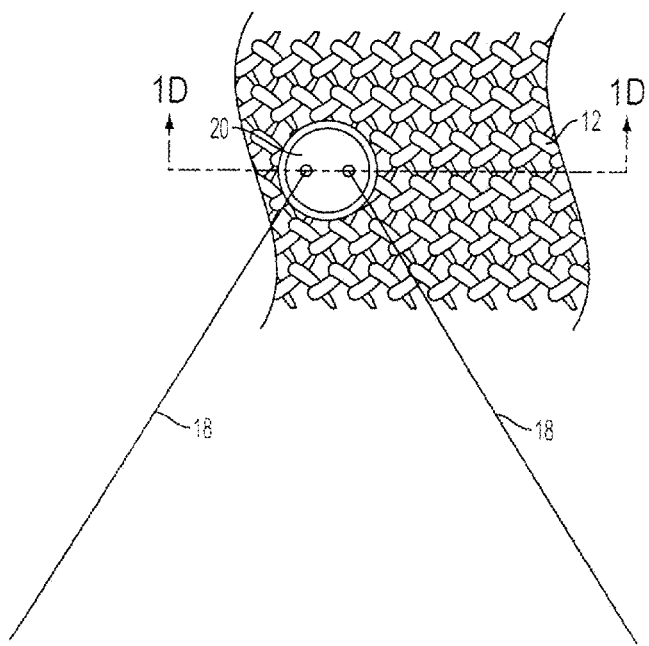
FIG. 1F is a partial plan view of the embodiment of the medical device shown in FIG. 1B, in accordance with systems and methods consistent with the present invention.

Referring to FIG. 1F, a partial plan view is shown of the embodiment of medical device 10 shown in FIG. 1B. In this view, the practitioner has cut cord 18 (assuming the integral embodiment of medical device 10) and slid aperture cover 20 along cord 18 in preparation to tie cords 18 snugly against aperture cover 20, creating the seating force to help hold medical device 10 in place. In this view, it is clear that the diameter of aperture 16 exceeds the diameter of any aperture in the regular pattern of apertures formed by the mesh strands in strip 12.

Figure 2A:
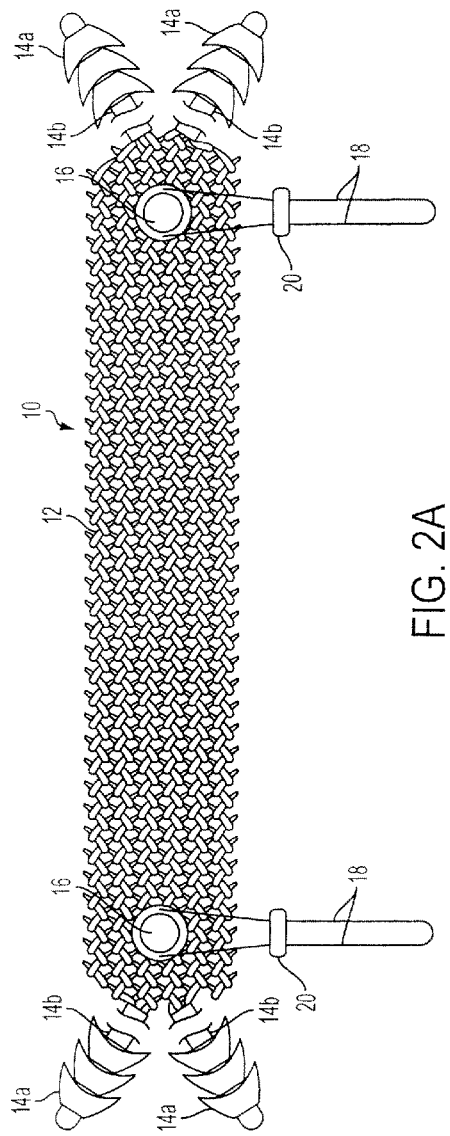
FIG. 2A is a plan view of another embodiment of a medical device for use in treatment of UI, in accordance with systems and methods consistent with the present invention.

Referring to FIG. 2A, a plan view is shown of another embodiment of medical device 10 for use in treatment of UI, in accordance with systems and methods consistent with the present invention. The embodiment of medical device 10 shown in FIG. 2A differs from the embodiment shown in FIGS. 1A-1F by including more than one fastener 14 on each end of strip 12. Moreover, in the embodiment of medical device 10 shown in FIG. 2A, each fastener 14 has an independent shaft 14b connected to an end of strip 12. The use of multiple fasteners 14 on one or more ends of strip 12 may be called for in certain circumstances. For example, a larger patient having a larger pelvis may require more support that may be provided through use of multiple fasteners 14 on one or more ends of strip 12.

Figure 2B:
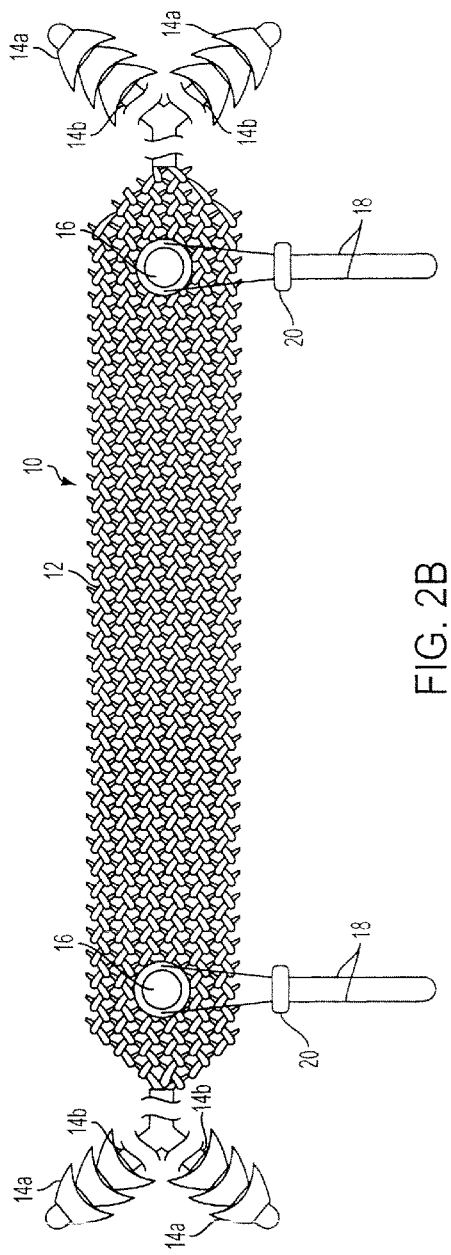
FIG. 2B is a plan view of another embodiment of a medical device for use in treatment of UI, in accordance with systems and methods consistent with the present invention.

Referring to FIG. 2B, a plan view is shown of another embodiment of medical device 10 for use in treatment of UI, in accordance with systems and methods consistent with the present invention. The embodiment of medical device 10 shown in FIG. 2B differs from the embodiment shown in FIGS. 1A-1F by including more than one fastener 14 on each end of strip 12. Moreover, in the embodiment of medical device 10 shown in FIG. 2B each fastener 14 has an independent shaft 14b connected to a common member that is connected to an end of strip 12. Again, the use of multiple fasteners 14 on one or more ends of strip 12 may be called for in certain circumstances.

Figure 3A:
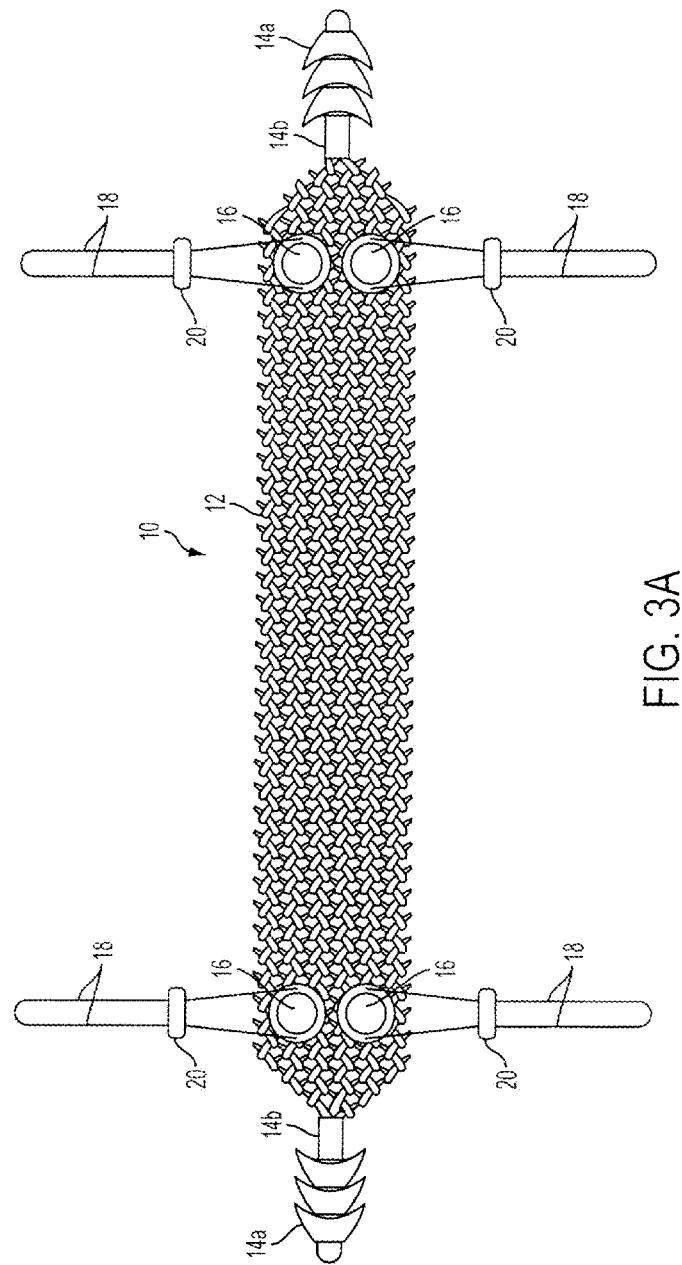
FIG. 3A is a plan view of another embodiment of a medical device for use in treatment of UI, in accordance with systems and methods consistent with the present invention.

Referring to FIG. 3A, a plan view is shown of another embodiment of medical device 10 for use in treatment of UI, in accordance with systems and methods consistent with the present invention. The embodiment of medical device 10 shown in FIG. 3A differs from the embodiment shown in FIGS. 1A-1F by including more than one aperture 16, more than one aperture cover 20 and more than one cord 18 in proximity to each end of strip 12. The use of more than one aperture 16, more than one aperture cover 20 and more than one cord 18 in proximity to each end of strip 12 may be called for in certain circumstances.

Figure 3B:
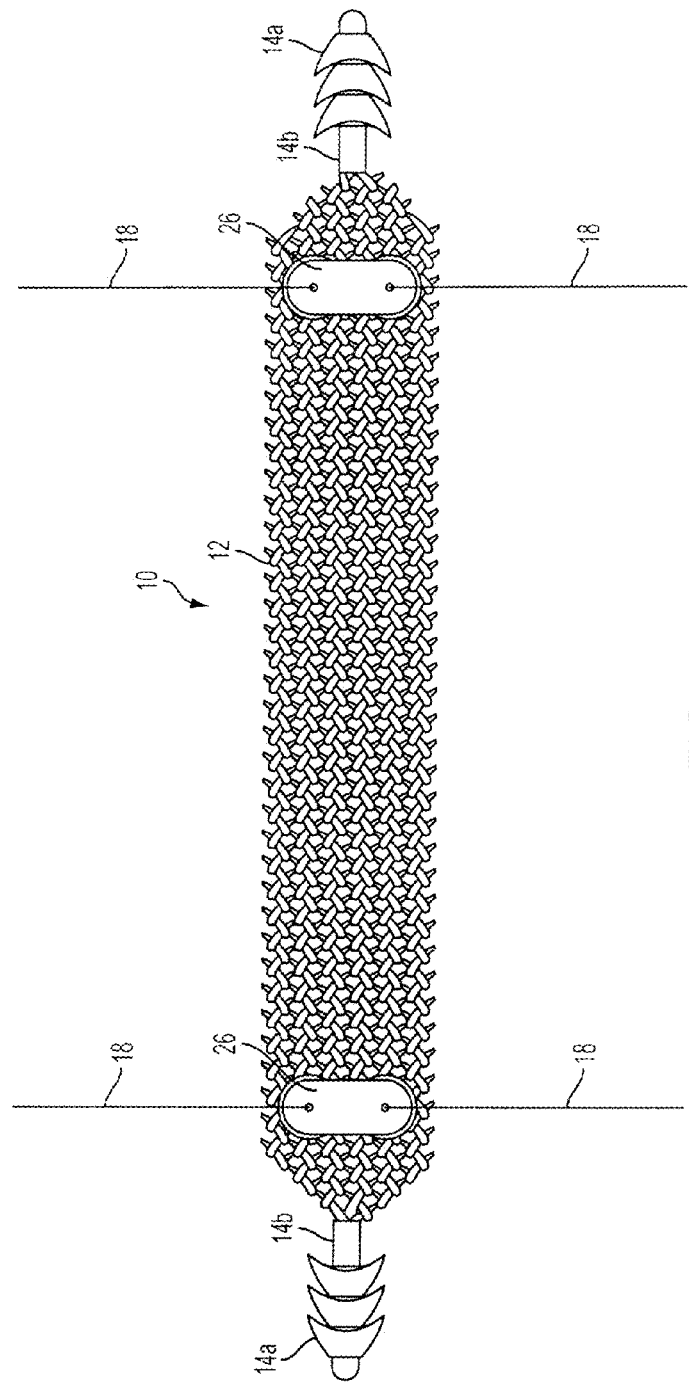
FIG. 3B is a plan view of another embodiment of a medical device for use in treatment of UI, in accordance with systems and methods consistent with the present invention.

Referring to FIG. 3B, a plan view is shown of another embodiment of medical device 10 for use in treatment of UI, in accordance with systems and methods consistent with the present invention. The embodiment of medical device 10 shown in FIG. 3B differs from the embodiment shown in FIGS. 1A-1F by including an aperture 16 and aperture cover 20 that is a shape other than circular (in this case, elliptical, though one may employ any desired shape) and located in proximity to each end of strip 12. The use of an elliptically-shaped aperture 16 and aperture cover 20 (or other shape) may improve holding strength, as compared to a circularly-shaped aperture 16 and aperture cover 20.

Figure 4A:
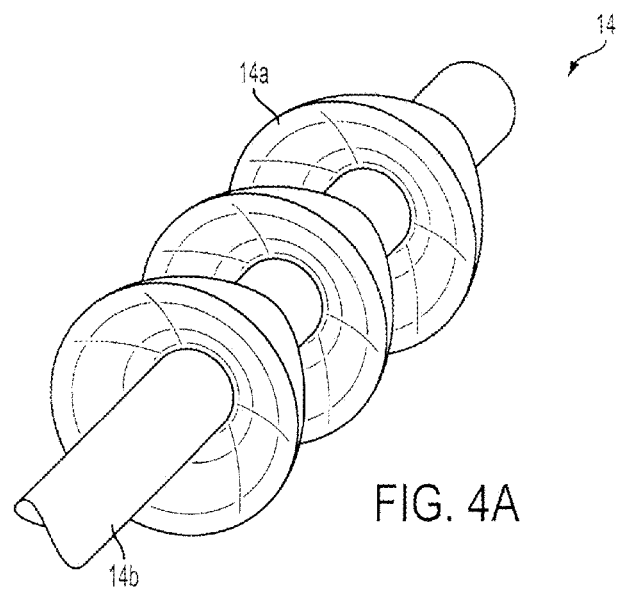
FIG. 4A is a partial perspective view of an embodiment of a fastener for use with any embodiment of a medical device for use in treatment of UI, in accordance with systems and methods consistent with the present invention.

Referring to FIG. 4A, a partial perspective view is shown of an embodiment of a fastener 14 for use with any embodiment of medical device 10 for use in treatment of UI, in accordance with systems and methods consistent with the present invention. Fastener 14, as shown in FIG. 4A, corresponds to fastener 14, as shown in FIGS. 1A-1C, FIGS. 2A-2B and FIGS. 3A-3B. Fastener 14 may include a shaft 14b coupled to an end of strip 12 (not shown) and one or more barbs 14a coupled to shaft 14b. As shown in FIG. 4A, fastener 14 includes a plurality of barbs 14a, however, a single barb 14a may be employed. Additionally, the barbs 14a shown in FIG. 4A traverse the entire perimeter of shaft 14b, however and more generally, fastener 14 and any other fastener that may be employed with medical device 10 may include one or more barbs that traverse only a portion of the perimeter of the respective shaft. Moreover, fastener 14 and any fastener that may be employed with medical device 10 are not limited to the exemplary structures shown in this or any other figure of the application. Simply put, fasteners used with medical device 10 may employ any structure suitable for anchoring the ends of strip 12 into patient tissue.

Figure 4B:
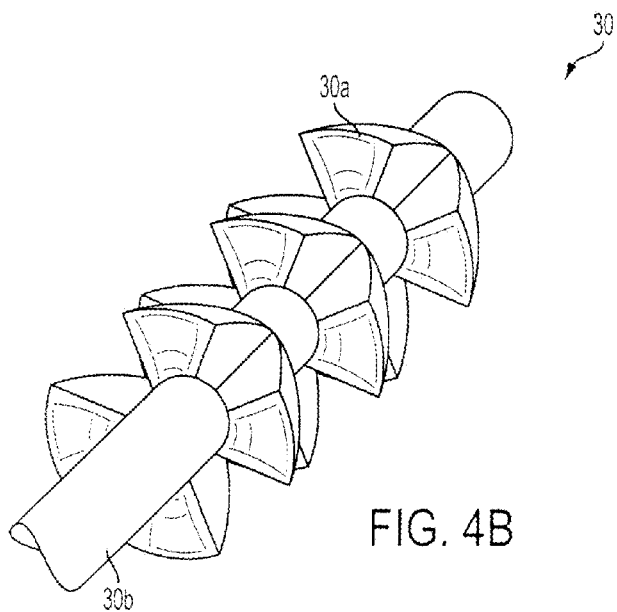
FIG. 4B is a partial perspective view of another embodiment of a fastener for use with any embodiment of a medical device for use in treatment of UI, in accordance with systems and methods consistent with the present invention.

Referring to FIG. 4B, a partial perspective view is shown of another embodiment of a fastener 30 for use with any embodiment of medical device 10 for use in treatment of UI, in accordance with systems and methods consistent with the present invention. Fastener 30 may include a shaft 30b coupled to an end of strip 12 (not shown) and one or more barbs 30a coupled to shaft 30b. As shown in FIG. 4B, fastener 30 includes a plurality of barbs 30a, however, a single barb 30a may be employed. Additionally, the barbs 30a shown in FIG. 4B traverse less than the entire perimeter of shaft 30b, however and more generally, fastener 30 and any other fastener that may be employed with medical device 10 may include one or more barbs that traverse a smaller portion of the perimeter of the respective shaft. Moreover, fastener 30 and any fastener that may be employed with medical device 10 are not limited to the exemplary structures shown in this or any other figure of the application. Simply put, fasteners used with medical device 10 may employ any structure suitable for anchoring the ends of strip 12 into patient tissue.

Referring to FIG. 4C, a partial perspective view is shown of another embodiment of a fastener 32 for use with any embodiment of medical device 10 for use in treatment of UI, in accordance with systems and methods consistent with the present invention. Fastener 32 may include a shaft 32b coupled to an end of strip 12 (not shown) and one or more barbs 32a coupled to shaft 32b. As shown in FIG. 4C, fastener 32 includes a plurality of barbs 32a, however, a single barb 32a may be employed. Additionally, the barbs 32a shown in FIG. 4C traverse less than the entire perimeter of shaft 32b, however and more generally, fastener 32 and any other fastener that may be employed with medical device 10 may include one or more barbs that traverse a smaller or greater portion of the perimeter of the respective shaft. Moreover, fastener 32 and any fastener that may be employed with medical device 10 are not limited to the exemplary structures shown in this or any other figure of the application. Simply put, fasteners used with medical device 10 may employ any structure suitable for anchoring the ends of strip 12 into patient tissue. Fastener 32 also represents an exemplary embodiment of a retractable fastener, as will be discussed below with reference to FIGS. 4D and 4E.

Figure 4D:
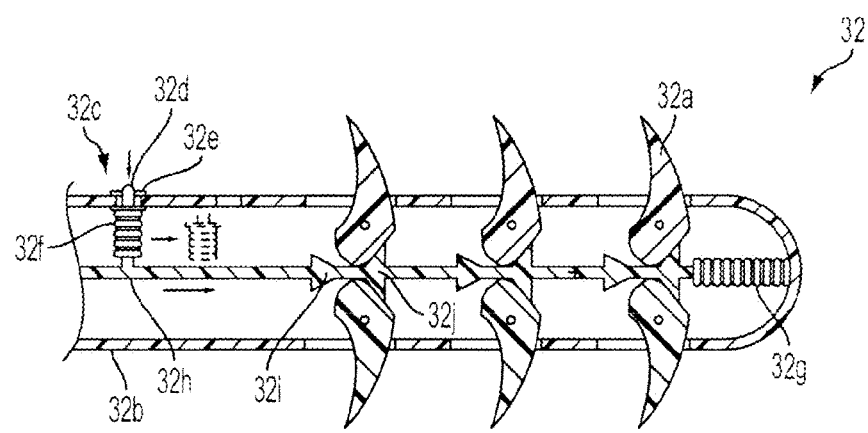
FIGS. 4D and 4E are cross sectional views taken along the line 4D-4D in FIG. 4C, showing an operational sequence for an embodiment of a retractable fastener, in accordance with systems and methods consistent with the present invention.
Figure 4E:
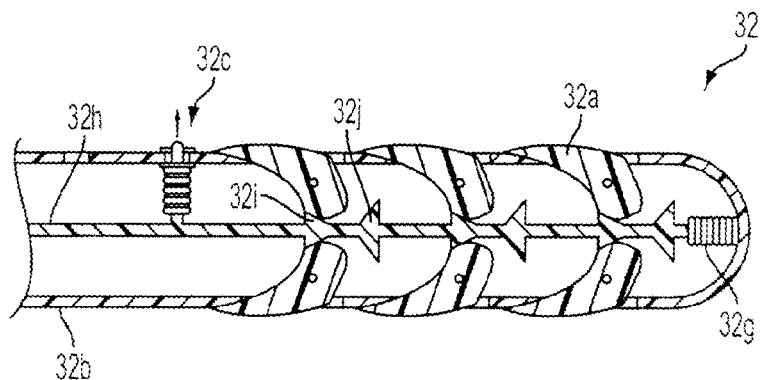

Referring to FIGS. 4D and 4E, cross sectional views are shown taken along the line 4D-4D in FIG. 4C, showing an operational sequence for an embodiment of a retractable barbed fastener 32, in accordance with systems and methods consistent with the present invention. In this exemplary embodiment, a system resides within shaft 32b for deploying and retracting barbs 32a. This system may include an operating mechanism 32c, a drive shaft 32h, barb actuators 32i and 32j and a biasing spring 32g. As shown in FIG. 4D, barbs 32a are deployed, in response to the default position of operating mechanism 32c and biasing spring 32g, i.e., the normal position of fastener 32 is open with barbs 32a deployed. Those skilled in the art appreciate that any retractable fastener employed with medical device 10 may alternatively have a normally closed or retracted fastener. Operating mechanism 32c may include an operating post 32d, a guide member 32e and a spring 32f.

To retract barbs 32a, a medical practitioner depresses operating post 32d such that it depresses spring 32f and moves operating post 32d below the interior wall of shaft 32b. As such guide member 32e, which does not move below the outer wall of shaft 32b, may be moved (to the right in FIG. 4D) along the outer surface of shaft 32b, while operating post 32d slides (to the right in FIG. 4D) within a slot cut into the interior wall of shaft 32b. The medical practitioner may employ a general purpose surgical instrument or a specifically-designed tool to operate operating mechanism 32c, as described, such a tool design being within the capability of those skilled in the art. As guide member 32e continues to move (to the right in FIG. 4D) along the outer surface of shaft 32b, it moves drive shaft 32h, which similarly moves barb actuators 32i and 32j (to the right in FIG. 4D) to compress spring 32g and retract barbs 32a. At a predetermined position located at the end of the interior guide slot for operating post 32d, operating post 32d reaches an aperture in shaft 32b, which frees operating post 32d to pop up in response to an expansion of spring 32f and barbs 32a are retracted, as shown in FIG. 4E.

Using FIG. 4E as a starting point to deploy or redeploy barbs 32a, the medical practitioner depresses operating post 32d such that it depresses spring 32f and moves operating post 32d below the interior wall of shaft 32b. The now-compressed biasing spring 32g expands, moving operating mechanism 32c (to the left in FIG. 4E) until reaching a predetermined position located at the opposing end of the interior guide slot for operating post 32d. At this point, operating post 32d reaches an aperture in shaft 32b, which frees operating post 32d to pop up in response to an expansion of spring 32f, deploying barbs 32a, as shown in FIG. 4D.

For the sake of clarity, the system set forth above for providing a retractable fastener 32 is merely exemplary. Moreover, it is well within the skills of persons in the art to create a wide variety of retractable fasteners, any of which may be employed with any embodiment of medical device 10.

Figure 4F:
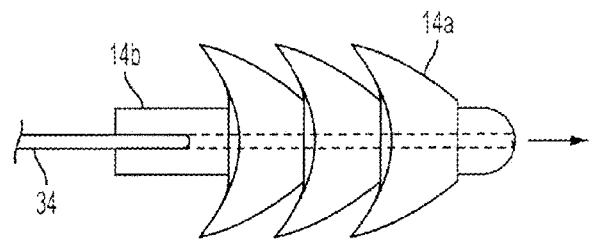
FIGS. 4F-4H are partial elevation views of embodiments of fasteners for use with any embodiment of a medical device for use in treatment of UI, in accordance with systems and methods consistent with the present invention.
Figure 4G:
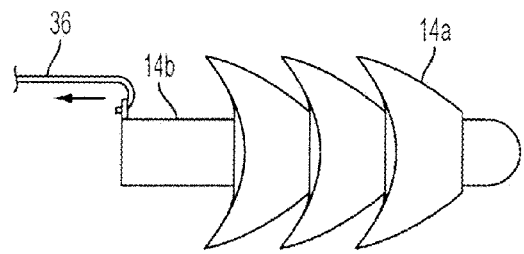
Figure 4H:
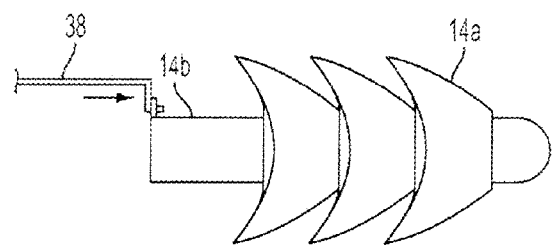

Referring to FIGS. 4F-4H, partial elevation views are shown of embodiments of fasteners 14 for use with any embodiment of medical device 10 for use in treatment of UI, in accordance with systems and methods consistent with the present invention. FIGS. 4F-4H also show exemplary tools 34-38 for inserting and/or extracting a fastener 14. In FIG. 4F, tool 34 is inserted within shaft 14b to drive barbs 14a into patient tissue, thereby inserting fastener 14. While not explicitly shown in FIG. 4F, those skilled in the art appreciate that tool 34 may be employed to disengage Fastener 14, as well, using any one of a variety of different designs within the level of experience of those skilled in the art. In FIG. 4G, tool 36 engages a position along shaft 14b for extracting fastener 14 (whether barbs 14 are retractable or not). In FIG. 4H, tool 38 engages a position along shaft 14b to drive barbs 14a into patient tissue, thereby inserting fastener 14. For the sake of clarity, the tools 34-38 set forth above for inserting and/or extracting fastener 14 (or any other fastener) are exemplary. Moreover, it is well within the skill level of those persons skilled in the art to create a wide variety of tools for inserting and/or extracting fastener 14 (or any other fastener), any of which may be employed with any embodiment of medical device 10.

Referring to FIG. 5A, a block diagram is shown of an embodiment of a system 40 for providing medical treatment, in accordance with systems and methods consistent with the present invention. System 40 may include any structure 42 that may be used for any medical purpose, including diagnosis, therapy, surgery or any other medical purpose for a patient. In an exemplary embodiment, structure 42 may comprise a strip of mesh for attachment to a patient under treatment for UI.

Structure 42 may be attached to the patient using fasteners 44, which are coupled to structure 42. Each fastener 44 may include one or more retractable barbs for attachment to the patient. The barbs may be retracted during insertion of fasteners 44 into the patient and then deployed for attachment to the patient. Having the barbs retracted during insertion of fasteners 44 will minimize patient trauma. If placement of the system 40 is deemed incorrect or otherwise undesired, the practitioner may remove system 40, without damage thereof, and then reattach system 40 to the patient. In this regard, the practitioner may remove system 40 either with the barbs deployed or retracted, however, retracting the barbs prior to removal will minimize patient trauma.

Referring to FIG. 5B, a side elevation view is shown of another embodiment of a system 46 for providing medical treatment, in accordance with systems and methods consistent with the present invention. System 46 may include any structure that may be used for any medical purpose, including diagnosis, therapy, surgery or any other medical purpose for a patient. In an exemplary embodiment, system 46 includes a strip 48 of mesh for attachment to a patient under treatment for UI. Mesh strip 48 differs from the other strips previously disclosed herein. For example, mesh strip 48 may not include one or more aperture covers 20, one or more cords 18 or one or more arrays of protrusions 22, as shown in FIGS. 1A-1C. If desired, however, mesh strip 48 could include any of these features or any others disclosed above.

Mesh strip 48 may be attached to a patient using fasteners 44, which are coupled to mesh strip 48. Each fastener 44 may include one or more retractable barbs for attachment to the patient. The barbs for system 46 may be employed, as described above with respect to system 40. System 46 may also include a cord 50 that is operably coupled to both fasteners 44 such that a practitioner may pull on cord 50, causing the barbs to retract and the fasteners 44 to be removed from a patient. A ring 52 may also be coupled to cord 50 for convenience when pulling on cord 50 to retract the barbs and remove fasteners 44.

Referring to FIG. 5C, a side elevation view is shown of another embodiment of a system 54 for providing medical treatment, in accordance with systems and methods consistent with the present invention. System 54 may include any structure that may be used for any medical purpose, including diagnosis, therapy, surgery or any other medical purpose for a patient. In an exemplary embodiment, system 54 includes a strip 48 of mesh for attachment to a patient under treatment for UI. As noted with respect to FIG. 5B, mesh strip 48 differs from the other strips previously disclosed herein. For example, mesh strip 48 does not include one or more aperture covers 20, one or more cords 18 or one or more arrays of protrusions 22, as shown in FIGS. 1A-1C. If desired, however, mesh strip 48 could include any of these features or any others disclosed above.

Mesh strip 48 may be attached to a patient using fasteners 44, which are coupled to mesh strip 48. Each fastener 44 may include one or more retractable barbs for attachment to the patient. The barbs for system 54 may be employed, as described above with respect to system 40. System 54 may also include a cord 50 that is coupled to each fastener 44, on a one-per-fastener basis, as shown. Each cord 50 may be operably coupled to a respective fastener 44 such that a practitioner may pull on cord 50, causing the respective barbs to retract and the respective fastener 44 to be removed from a patient. A ring 52 may also be coupled to each cord 50 for convenience when pulling on a respective cord 50 to retract the associated barbs and remove the respective fastener 44.

Figure 5D:
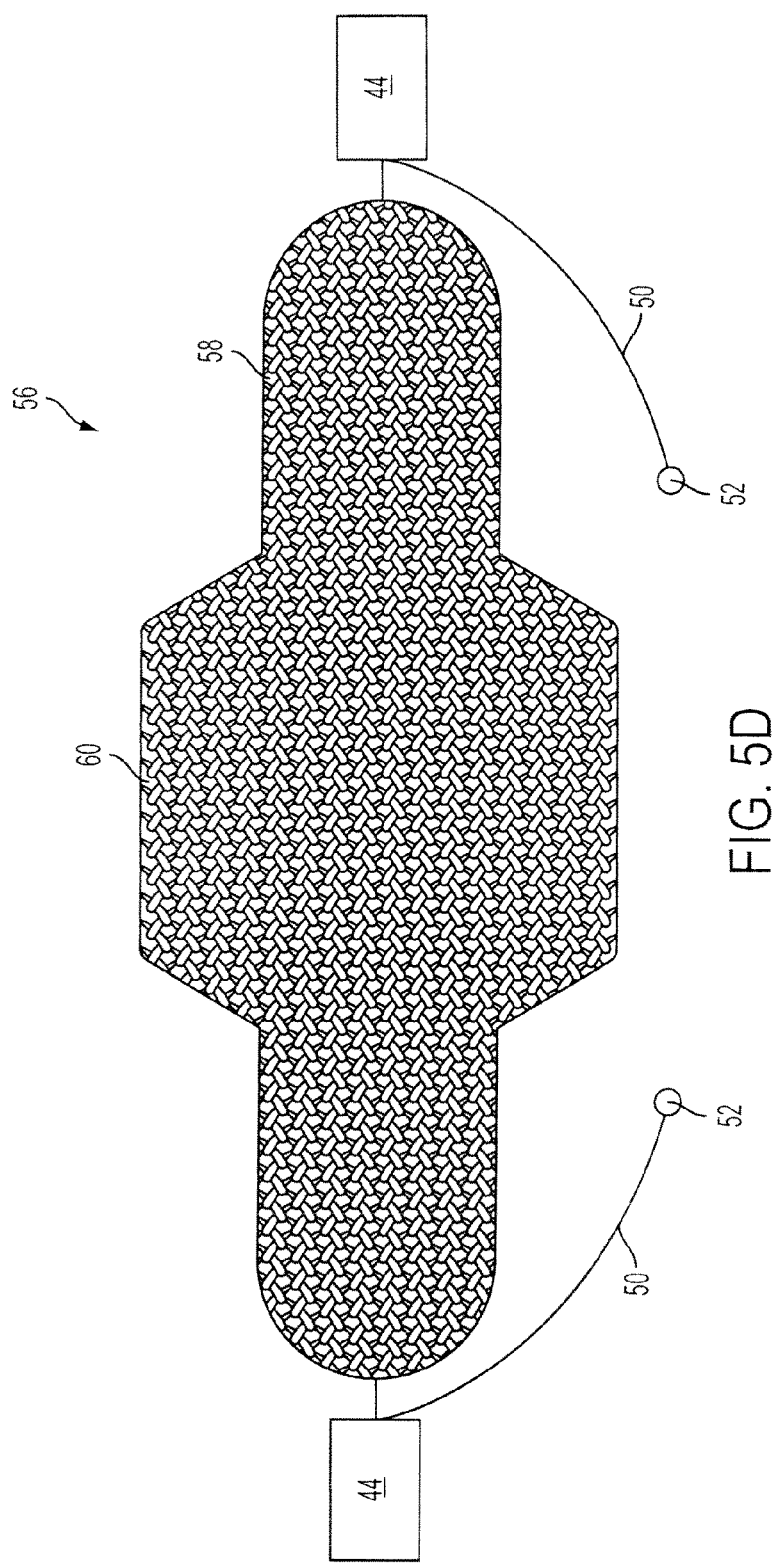
FIG. 5D is a plan view of another embodiment of a system for providing medical treatment, in accordance with systems and methods consistent with the present invention.

Referring to FIGS. 5D and 5E, plan views are shown of other embodiments of systems 56 and 62, respectively, for providing medical treatment, in accordance with systems and methods consistent with the present invention. Systems 56 and 62 are analogous to system 54, as shown in FIG. 5C, as each fastener 44 is coupled to a dedicated cord 50 and ring 52 for barb retraction and fastener removal.

The plan view of FIG. 5D shows that the mesh strip 58 includes a portion 60 of maximum width between the first end of the strip 58 and the second end of the strip 58. Wider portion 60 has a length parallel to the primary axis of the strip 58 that constitutes less than half the distance between the first end of the strip 58 and the second end of the strip 58. Wider portion 60 affords greater surface area contact and support of a patient's urethra, once the strip 58 is attached beneath the urethra for treatment of UI, as described herein. The greater surface area contact and support associated with strip 58 is apparent when comparing the planar view of the strip 58 against the planar view of existing mesh strips, which have a basic linear shape as depicted in FIG. 1A (although without the apertures 16).

As shown in FIG. 5E, the strip 61 also includes a wider portion between the ends of the strip 61, which in this case is simply the midpoint since the strip 61 has an elliptical shape. As such, the strip 61 similarly provides greater surface area contact and support of a patient's urethra, once the strip 61 is attached beneath the urethra. Other shapes and configurations of mesh strips may be employed, as long as a portion of maximum width is between the first end of the strip and the second end of the strip and this wider portion has a length parallel to the primary axis of the strip that constitutes less than half the distance between the first end of the strip and the second end of the strip. This manner of increasing surface area contact and support of a patient's urethra may be employed with any system or method set forth herein.

While an exemplary embodiment for providing a retractable fastener 14 or 44 was previously set forth above in connection with the description of FIGS. 4C-4E, those skilled in the art understand that retractable fasteners 14 or 44 may be constructed in any one of a variety of different ways. Described below with respect to FIGS. 6-11 are a series of additional exemplary embodiments for providing fasteners 14 or 44 that are retractable. The fasteners shown in FIGS. 6-11 are identified using specific reference numbers 64, 94, 120, 152, 162 and 180 which differ from the general reference numbers used elsewhere herein to represent fasteners, i.e., 14 or 44. This numbering convention is intended to indicate that there are several different fastener embodiments and that any fastener embodiment may be utilized in any combination with any system described herein.

Regarding FIG. 6A, a side elevation view is shown of an embodiment of a fastener 64 for use in a system for providing medical treatment, in accordance with systems and methods consistent with the present invention. Fastener 64 may include a shaft 66 including one or more apertures 68 for allowing passage of one or more retractable barbs 82 and 84. Fastener 64 may include a conical front portion 70 and a tip 72 of a size and shape to minimize resistance from insertion of fastener 64 into a patient. A cord 50 and a ring 52 may be coupled to fastener 64 to facilitate removal of fastener 64, if and when desired. The three dots shown in-line with cord 50 indicate that cord 50 may have any desired length, however, cord 50 is generally long enough for a practitioner to easily find ring 52 for removal of fastener 64, if desired.

While shaft 66 may have any desired shape, in an exemplary embodiment, shaft 66 may include a generally tubular base portion coupled to a conical front portion 70, as shown. Additionally, shaft 66 may be manufactured to any desired size or dimension, however, in an exemplary embodiment, the length of shaft 66 (from the end of the base to the tip 72) may fall in the range of 0.25 of an inch to 1.5 inches and the outer diameter of shaft 66 may fall in the range of 0.005 to 0.350 of an inch. The remaining fastener components, as shown in FIGS. 6B-6D, may be sized to be generally proportional to the overall length and width of shaft 66. Shaft 66 may also comprise an integrally formed structure made of any material suitable for patient implantation, such as a plastic.

Referring to FIG. 6B, the remaining fastener components are shown. A retractable barb member 74 (or member 74) may comprise an integral structure having a shaft 76 coupled to a pair of arms 78 and 80 and retractable barbs 84 and 82, respectively. Member 74 may be biased to push arms 78 and 80 away from each other. While member 74 may comprise an integral structure, those skilled in the art understand that member 74 may comprise multiple parts, e.g., a pair of separate arms coupled together at a common point, such as the apex, and having means for providing force to move the arms apart. An interior wall 90 includes an aperture 92, as shown in FIG. 6G (this cross section view removes member 74 to show aperture 92), to properly align member 74 such that the retractable barbs 82 and 84 are aligned for selective passage through one or more apertures 68. Arms 78 and 80 may also include support fins 86 and 88 for support against an interior surface of shaft 66 when the retractable barbs 82 and 84 are deployed, as shown in FIG. 6D.

Figure 12A:
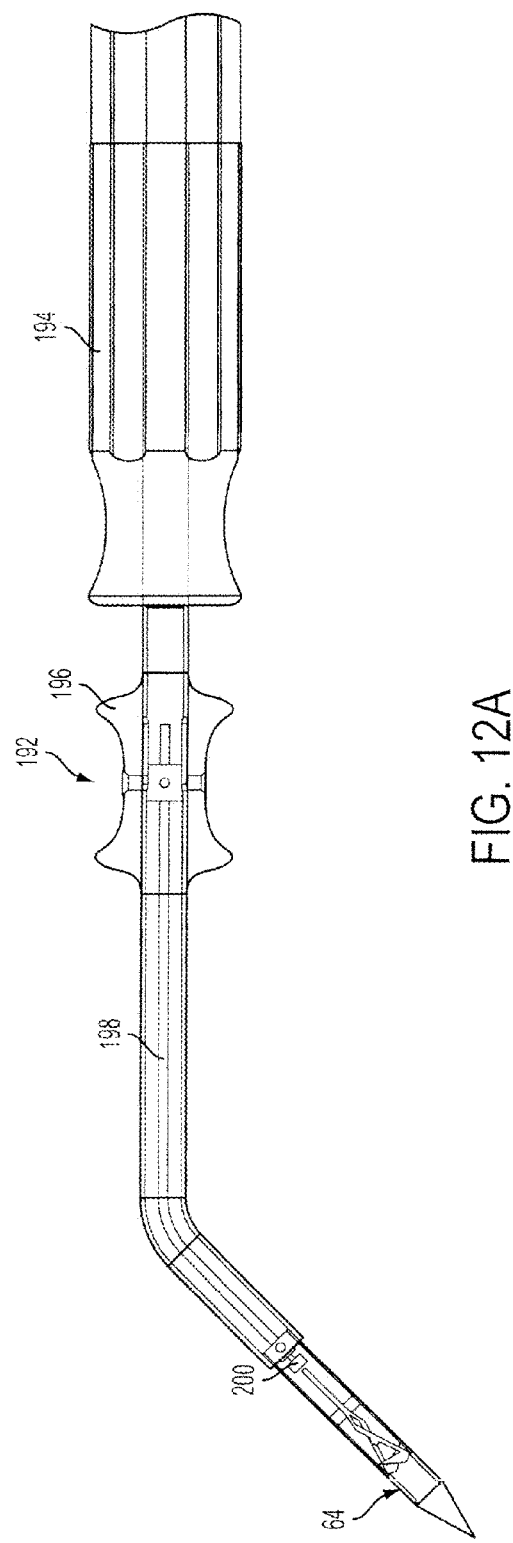
FIGS. 12A and 12B are a sequence of side elevation views of an embodiment of a tool for inserting a fastener, in accordance with systems and methods consistent with the present invention. In this exemplary sequence, the fastener embodiment from FIGS. 6A-6G is first shown with the retractable barbs stowed in FIG. 12A and then deployed in FIG. 12B.
Figure 12B:
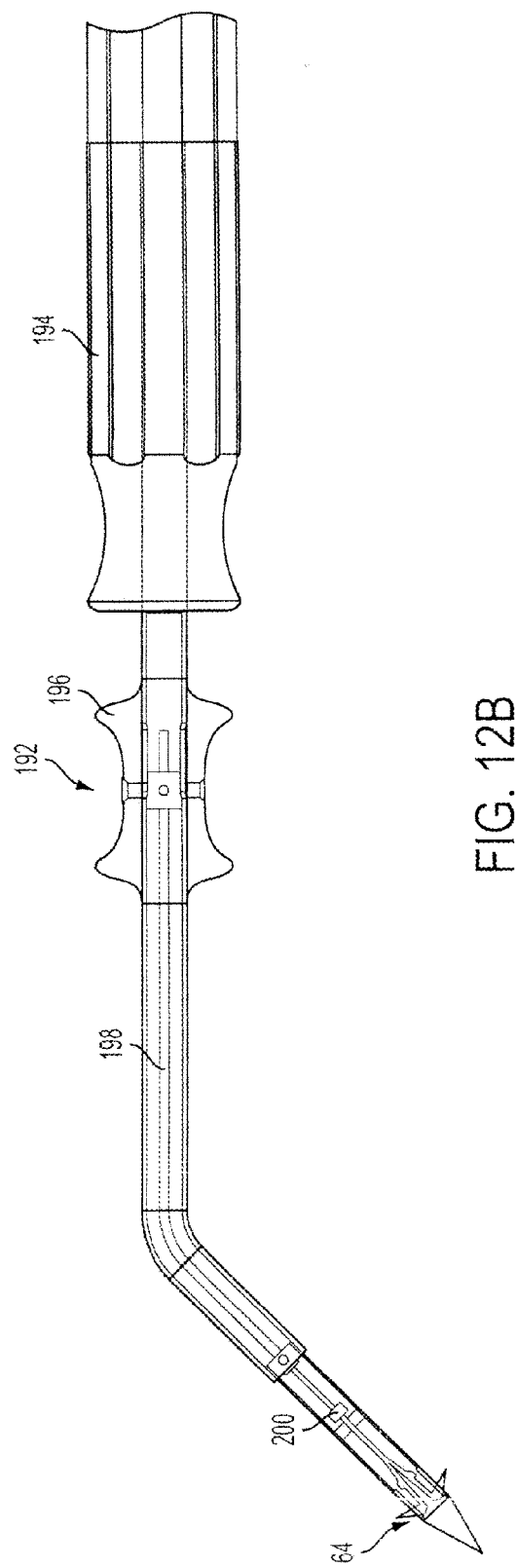

Referring to FIGS. 6B-6D, a sequence of side elevation views demonstrate a manner of deploying the retractable barbs 82 and 84 of the embodiment of fastener 64. FIG. 6B depicts the retractable barbs 82 and 84 in an initial retracted position. From this condition, a practitioner may insert a tool (not shown here, however, an exemplary tool 192 is shown in FIGS. 12A and 12B and described below) in through the opening in the base of shaft 66 to apply force against shaft 76 and move member 74 toward tip 72, causing the retractable barbs 82 and 84 to move apart and pass through apertures 68 into a deployed position, as shown in FIG. 6D. As is evident from FIGS. 6B-6D, in order for the retractable barbs 82 and 84 to transition between the stowed and deployed positions and vice versa, arms 78 and 80, which swing across each other as shown during the transition, may be offset from each other such that they are generally not coplanar.

Figure 14:
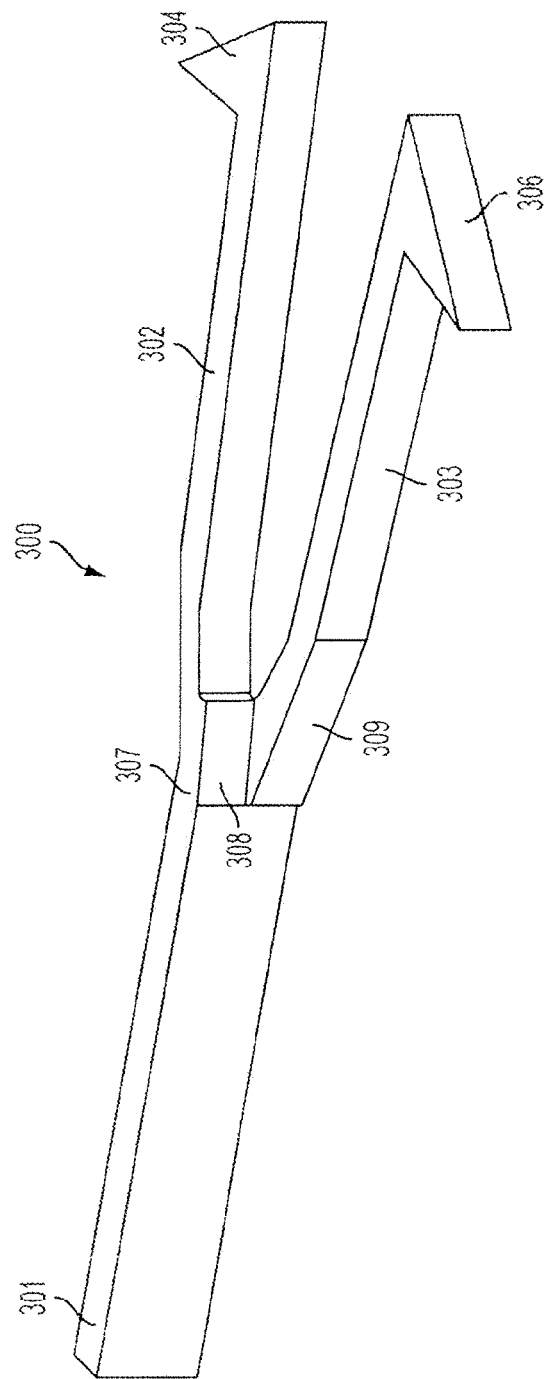
FIG. 14 is a perspective view of an embodiment of a retractable barb member for use with the fastener embodiment depicted in FIGS. 6A-6G.

This aspect of retractable member 74 is also shown in a further embodiment of a retractable barb member 300 (or member 300), as shown in FIG. 14. Member 300 is largely similar to member 74 and may be employed in a fastener embodiment similar to fastener 64, as shown in FIGS. 6A-6G. In particular, member 300 includes a shaft 301 coupled to arms 302 and 303 and retractable barbs 304 and 306, respectively. Like member 74, member 300 may be biased such that arms 302 and 303 may move apart from one another into a deployed state, as shown in FIG. 14. Saying that member 300 may be biased such that arms 302 and 303 may move apart from one another into a deployed state means that arms 302 and 303 may move apart from one another unless restricted from doing so, such as from having member 300 stowed in a fastener shaft, like that shown in FIG. 6B. As is evident from FIG. 14, arms 302 and 303 are generally not coplanar, allowing them to swing across one another during barb deployment and stowage operations. In proximity to a point of intersection 307 between shaft 301 and arms 302 and 303 are regions 308 and 309 that may provide a cam action during barb stowage. While member 300 is largely similar to member 74, member 300 does not include the support fins 86 and 88, as shown in FIGS. 6B-6D, however, outer surfaces of each arm 302 and 303 may provide this support function, resting in contact with an internal shaft surface once deployed.

FIGS. 12A and 12B show a sequence of side elevation views of an embodiment of a tool 192 for inserting fastener 64, in accordance with systems and methods consistent with the present invention. In this exemplary sequence, fastener 64 is first shown with the barbs 82 and 84 stowed in FIG. 12A and then deployed in FIG. 12B. Tool 192 may include a handle 194, an actuator 196 coupled to a shaft 198 for moving a driver 200 against shaft 76 of fastener 64.

Typically, the practitioner will have inserted fastener 64 into the patient with a tool, such as tool 192, that may be placed around the edge of the base of shaft 66 to apply force against the base edge (this prevents inadvertent barb deployment while inserting fastener 64 into patient). During the insertion of fastener 64 into the patient, the retractable barbs 82 and 84 are typically left in the retracted or stowed position, as shown in FIG. 6B, to limit patient trauma during fastener insertion. Once inserted, the retractable barbs 82 and 84 may be deployed, as described above. Assuming the practitioner is not satisfied with the placement of fastener 64 or its related medical structure (not shown, but analogous to any such structure shown in any system embodiment described herein), the practitioner may remove the system (i.e., the medical structure and its related barb or barbs) without damage thereto or to the patient and then reattach the system in the desired location.

Figure 13:
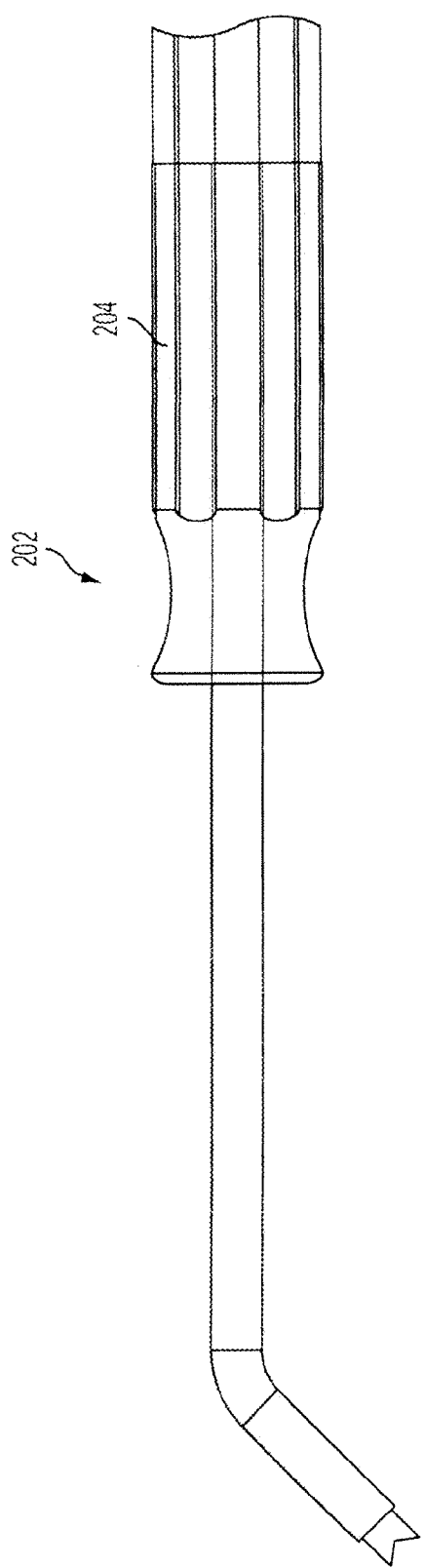
FIG. 13 is a side elevation view of an embodiment of a tool for removing a fastener, in accordance with systems and methods consistent with the present invention.

To remove the system, the practitioner may employ tool 202, as shown in FIG. 13. Tool 202 is an exemplary embodiment of a removal tool and those skilled in the art understand the other tool designs will suffice. In operation, the practitioner may locate ring 52 for fastener 64 an pull it taught, taking care not to move fastener 64 while the retractable barbs 82 and 84 are deployed. Then, the practitioner may engage the cord 50 with the slot located in the tip of tool 202, so that the practitioner may easily guide the tool tip up to the base of shaft 66. In this position, the practitioner may apply a holding force against the base of shaft 66, while the practitioner pulls back on ring 52, thereby drawing member 74 back to the stowed position, as shown in FIG. 6B. Once the retractable barbs 82 and 84 are stowed, the practitioner may remove tool 202 and pull on ring 52 to remove fastener 64, while minimizing patient trauma with retracted barbs 82 and 84. Assuming other fasteners 64 are included with the subject system, the practitioner may similarly remove them and the related medical structure, intact and undamaged, for reuse.

Regarding FIG. 7A, a side elevation view is shown of an embodiment of a fastener 94 for use in a system for providing medical treatment, in accordance with systems and methods consistent with the present invention. Fastener 94 may include a shaft 96 including one or more apertures 98 for allowing passage of one or more retractable barbs 110 and 112. Fastener 94 may include a conical front portion 100 and a tip 102 of a size and shape to minimize resistance from insertion of fastener 94 into a patient. A cord 50 and a ring 52 may be coupled to fastener 94 to facilitate removal of fastener 94, if and when desired. The three dots shown in-line with cord 50 indicate that cord 50 may have any desired length, however, cord 50 is generally long enough for a practitioner to easily find ring 52 for removal of fastener 94, if desired.

While shaft 96 may have any desired shape, in an exemplary embodiment, shaft 96 may include a generally tubular base portion coupled to a conical front portion 100, as shown. Additionally, shaft 96 may be manufactured to any desired size or dimension, however, in an exemplary embodiment, the length of shaft 96 (from the end of the base to the tip 102) may fall in the range of 0.25 of an inch to 1.5 inches and the outer diameter of shaft 96 may fall in the range of 0.005 to 0.350 of an inch. The remaining fastener components, as shown in FIGS. 7B-7D, may be sized to be generally proportional to the overall length and width of shaft 96. Shaft 96 may also comprise an integrally formed structure made of any material suitable for patient implantation, such as a plastic.

Referring to FIG. 7B, the remaining fastener components are shown. A retractable barb member 104 (or member 104) may comprise an integral structure having a pair of arms 106 and 108 and retractable barbs 110 and 112, respectively. Member 104 may comprise an integral piece of material, such as a plastic, formed into arms 106 and 108 and the respective retractable barbs 110 and 112, the two arms being coupled at an apex and biased to pull arms 106 and 108 toward each other. Appropriate biasing may determine the initial condition (stowed) of the retractable barbs 110 and 112, such that they remain stowed within shaft 96. While member 104 may comprise an integral structure, those skilled in the art understand that member 104 may comprise multiple parts, e.g., a pair of separate arms coupled together at a common point, such as the apex, and having means for providing force to move the arms toward each other. As shown in FIG. 7B, a first portion of member 104 contacts the interior of shaft 96 in proximity to tip 102, while the opposing portion of member 104 comprising the retractable barbs 110 and 112 rests against an actuator 116. Actuator 116 may be coupled to a rotatable shaft 114, which may be supported by interior shaft wall 118 including a threaded aperture to accommodate rotatable shaft 114.

Referring to FIGS. 7B-7D, a sequence of side elevation views demonstrate a manner of deploying the retractable barbs 110 and 112 of the embodiment of fastener 94. FIG. 7B depicts the retractable barbs 110 and 112 in an initial retracted position. From this condition, a practitioner would insert a tool (not shown) in through the opening in the base of shaft 96 to engage the head of rotatable shaft 114 and rotate it. Rotation of shaft 114 causes linear translation of actuator 116 toward the apex of member 104, causing the retractable barbs 110 and 112 to move apart and pass through apertures 98 into a deployed position, as shown in FIG. 7D. The practitioner may pull back on ring 52 to apply a counterforce during the deployment of the retractable barbs 110 and 112, to maintain fastener position. Indeed, this technique may be employed with any embodiment disclosed herein.

Typically, the practitioner will have inserted fastener 94 into the patient with a tool (not shown) that may be applied around the edge of shaft 96. During the insertion of fastener 94 into the patient, the retractable barbs 110 and 112 are typically left in the retracted or stowed position, as shown in FIG. 7B, to limit patient trauma during fastener insertion. Once inserted, the retractable barbs 110 and 112 may be deployed, as described above. Assuming the practitioner is not satisfied with the placement of fastener 94 or its related medical structure (not shown, but analogous to any such structure shown in any system embodiment described herein), the practitioner may remove the system (i.e., the medical structure and its related barb or barbs) without damage thereto or to the patient and then reattach the system in the desired location.

To remove the system, the practitioner may employ tool 202, as shown in FIG. 13. In operation, the practitioner may locate ring 52 for fastener 94 and pull it taught, taking care not to move fastener 94 while the retractable barbs 110 and 112 are deployed. Then, the practitioner may engage the cord 50 with the slot located in the tip of tool 202, so that the practitioner may easily guide the tool tip up to the base of shaft 96. In this position, the practitioner may apply a holding force against the base of shaft 96, while a second tool is inserted into shaft 96, as previously described, to engage shaft 114. Shaft 114 may then be rotated to reverse translation of shaft 114, thereby moving actuator 116 back to the stowed position, as shown in FIG. 7B. As actuator 116 retracts, the retractable barbs 110 and 112 return to the retracted position, as shown in FIG. 7B, due to the biasing of member 104 to pull arms 106 and 108 towards one another. Once the retractable barbs 110 and 112 are stowed, the practitioner may remove tool 202 and pull on ring 52 to remove fastener 94, while minimizing patient trauma with retracted barbs 110 and 112. Assuming other fasteners 94 are included with the subject system, the practitioner may similarly remove them and the related medical structure, intact and undamaged, for reuse.

Regarding FIG. 8A, a side elevation view is shown of an embodiment of a fastener 120 for use in a system for providing medical treatment, in accordance with systems and methods consistent with the present invention. Fastener 120 may include a shaft 122 including one or more apertures 124 for allowing passage of one or more retractable barbs 136 and 138. Fastener 120 may include a conical front portion 126 and a tip 128 of a size and shape to minimize resistance from insertion of fastener 120 into a patient. A cord 50 and a ring 52 may be coupled to fastener 120 to facilitate removal of fastener 120, if and when desired. The three dots shown in-line with cord 50 indicate that cord 50 may have any desired length, however, cord 50 is generally long enough for a practitioner to easily find ring 52 for removal of fastener 120, if desired.

While shaft 122 may have any desired shape, in an exemplary embodiment, shaft 122 may include a generally tubular base portion coupled to a conical front portion 126, as shown. Additionally, shaft 122 may be manufactured to any desired size or dimension, however, in an exemplary embodiment, the length of shaft 122 (from the end of the base to the tip 128) may fall in the range of 0.25 of an inch to 1.5 inches and the outer diameter of shaft 122 may fall in the range of 0.005 to 0.350 of an inch. The remaining fastener components, as shown in FIGS. 8B-8D, may be sized to be generally proportional to the overall length and width of shaft 122. Shaft 122 may also comprise an integrally formed structure made of any material suitable for patient implantation, such as a plastic.

Referring to FIG. 8B, the remaining fastener components are shown. A retractable barb member 130 (or member 130) may comprise an integral structure having a pair of arms 132 and 134 and retractable barbs 136 and 138, respectively. Member 130 may comprise an integral piece of material, such as a plastic, formed into arms 132 and 134 and the respective retractable barbs 136 and 138, the two arms being coupled at an apex and biased to pull arms 132 and 134 toward each other. Appropriate biasing may determine the initial condition (stowed) of the retractable barbs 136 and 138, such that they remain stowed within shaft 122. While member 130 may comprise an integral structure, those skilled in the art understand that member 130 may comprise multiple parts, e.g., a pair of separate arms coupled together at a common point, such as the apex, and having means for providing force to move the arms toward each other. As shown in FIG. 8B, a first portion of member 130 contacts the interior of shaft 122 in proximity to tip 128, while the opposing portion of member 130 comprising the retractable barbs 136 and 138 rests against an actuator 150. Actuator 150 may be coupled to a shaft 140, which may be supported by interior shaft wall 142 including an aperture to accommodate shaft 140. Shaft 140 may include a pair of detents 146 and 148 for holding shaft 140 in a retracted position (detent 148) or a deployed position (detent 146).

Referring to FIGS. 8B-8D, a sequence of side elevation views demonstrate a manner of deploying the retractable barbs 136 and 138 of the embodiment of fastener 120. FIG. 8B depicts the retractable barbs 136 and 138 in an initial retracted position. From this condition, a practitioner would insert a tool (not shown) in through the opening in the base of shaft 122 to engage and push against the end of shaft 140. Pushing the tool against the end of shaft 140 with sufficient force will exceed the holding force associated with detent 148, thereby allowing movement of actuator 150 toward the apex of member 130, causing the retractable barbs 136 and 138 to move apart and pass through apertures 124 into a deployed position, as shown in FIG. 8D. In the deployed position, detent 146 will have engaged interior shaft wall 142, thereby holding retractable barbs 136 and 138 in a deployed position. An additional ring 52 and cord 50 may be coupled to shaft 122 so the practitioner may pull back on this ring 52 to apply a counterforce during the deployment of the retractable barbs 136 and 138 which maintains fastener position.

Typically, the practitioner will have inserted fastener 120 into the patient with a tool (not shown) that may be applied around the base edge (to prevent inadvertent barb deployment while inserting fastener 120 into patient). During the insertion of fastener 120 into the patient, the retractable barbs 136 and 138 are typically left in the retracted or stowed position, as shown in FIG. 8B, to limit patient trauma during fastener insertion. Once inserted, the retractable barbs 136 and 138 may be deployed, as described above. Assuming the practitioner is not satisfied with the placement of fastener 120 or its related medical structure (not shown, but analogous to any such structure shown in any system embodiment described herein), the practitioner may remove the system (i.e., the medical structure and its related barb or barbs) without damage thereto or to the patient and then reattach the system in the desired location.

To remove the system, the practitioner may employ tool 202, as shown in FIG. 13. In operation, the practitioner may locate ring 52 for fastener 120 an pull it taught, taking care not to move fastener 120 while the retractable barbs 136 and 138 are deployed. Then, the practitioner may engage the cord 50 with the slot located in the tip of tool 202, so that the practitioner may easily guide the tool tip up to the base of shaft 122. In this position, the practitioner may apply a holding force against the base of shaft 122, while pulling on ring 52 to move actuator 150 back to the stowed position, as shown in FIG. 8B. As actuator 150 retracts, the retractable barbs 136 and 138 return to the retracted position, as shown in FIG. 8B, due to the biasing of member 130 to pull arms 132 and 134 towards one another. Once the retractable barbs 136 are stowed, the practitioner may remove tool 202 and pull on ring 52 to remove fastener 120, while minimizing patient trauma with retracted barbs 136 and 138. Assuming other fasteners 120 are included with the subject system, the practitioner may similarly remove them and the related medical structure, intact and undamaged, for reuse.

Regarding FIG. 9A, a side elevation view is shown of an embodiment of a fastener 152 for use in a system for providing medical treatment, in accordance with systems and methods consistent with the present invention. Fastener 152 may include a shaft 154 having one or more thinned portions 160 forming one or more living hinges that may be selectively employed to form a retractable barb on an end of shaft 154. Fastener 152 may include a conical front portion 157 and a tip 158 of a size and shape to minimize resistance from insertion of fastener 152 into a patient. A cord 50 and a ring 52 may be coupled to fastener 152 to facilitate removal of fastener 152, if and when desired. The three dots shown in-line with cord 50 indicate that cord 50 may have any desired length, however, cord 50 is generally long enough for a practitioner to easily find ring 52 for removal of fastener 152, if desired.

While shaft 154 may have any desired shape, in an exemplary embodiment, shaft 154 may include a generally tubular base portion coupled to a conical front portion 157, as shown. Additionally, shaft 154 may be manufactured to any desired size or dimension, however, in an exemplary embodiment, the length of shaft 154 (from the end of the base to the tip 158) may fall in the range of 0.25 of an inch to 1.5 inches and the outer diameter of shaft 154 may fall in the range of 0.005 to 0.350 of an inch. The remaining fastener components, as shown in FIGS. 9B-9D, may be sized to be generally proportional to the overall length and width of shaft 154. Shaft 154 may also comprise an integrally formed structure made of any material suitable for patient implantation, such as a plastic.

Referring to FIG. 9B, the remaining fastener components are shown. A shaft 161 may be rotatably coupled at one end to a bearing located near the tip 158 and on the inside of shaft 154. An interior wall 158 including a threaded aperture provides further support to shaft 161. The opposite end of shaft 161 provides a position for a tool to engage and rotate shaft 161 to selectively deploy and retract the retractable barb formed by the leading end of shaft 154.

Referring to FIGS. 9B-9D, a sequence of side elevation views demonstrate a manner of deploying the retractable barb formed by the leading end of shaft 154. FIG. 9B depicts the retractable barb in an initial retracted position. From this condition, a practitioner would insert a tool (not shown) in through the opening in the base of shaft 154 to engage the head of shaft 161 and rotate it. Rotation of shaft 161 causes a linear translation that pulls tip 158 toward the base of shaft 154, causing the living hinges formed by thinned portions 160 to deform, as shown in FIGS. 9C and 9D. Once the translation is complete, the retractable barb is formed (or deployed) by the end of shaft 154, as shown in FIG. 9D. The practitioner may pull back on ring 52 to apply a counterforce during the deployment of the retractable barb which maintains fastener position.

Typically, the practitioner will have inserted fastener 152 into the patient with a tool (not shown) that may be applied around the edge of the base. During the insertion of fastener 152 into the patient, the retractable barb is typically left in the retracted or stowed position, as shown in FIG. 9B, to limit patient trauma during fastener insertion. Once inserted, the retractable barb may be deployed, as described above. Assuming the practitioner is not satisfied with the placement of fastener 152 or its related medical structure (not shown, but analogous to any such structure shown in any system embodiment described herein), the practitioner may remove the system (i.e., the medical structure and its related barb or barbs) without damage thereto or to the patient and then reattach the system in the desired location.

To remove the system, the practitioner may employ tool 202, as shown in FIG. 13. In operation, the practitioner may locate ring 52 for fastener 152 an pull it taught, taking care not to move fastener 152 while the retractable barb is deployed. Then, the practitioner may engage the cord 50 with the slot located in the tip of tool 202, so that the practitioner may easily guide the tool tip up to the base of shaft 154. In this position, the practitioner may apply a holding force against the base of shaft 154, while a second tool is inserted into shaft 154, as previously described, to engage the head of shaft 161. Shaft 161 may then be rotated to reverse translation of shaft 161, pushing toward the tip 158 of shaft 154 and returning shaft 154 to its initial configuration, as shown in FIG. 9B in which the barb is retracted. Once the barb is retracted, the practitioner may remove tool 202 and pull on ring 52 to remove fastener 152, while minimizing patient trauma with retracted barb. Assuming other fasteners 152 are included with the subject system, the practitioner may similarly remove them and the related medical structure, intact and undamaged, for reuse.

Regarding FIG. 10A, a side elevation view is shown of an embodiment of a fastener 162 for use in a system for providing medical treatment, in accordance with systems and methods consistent with the present invention. Fastener 162 may include a shaft 164 having one or more thinned portions 170 forming one or more living hinges that may be selectively employed to form a retractable barb on an end of shaft 164. Fastener 162 may include a conical front portion 168 and a tip 166 of a size and shape to minimize resistance from insertion of fastener 162 into a patient. A cord 50 and a ring 52 may be coupled to fastener 162 to facilitate barb deployment. The three dots shown in-line with cord 50 indicate that cord 50 may have any desired length, however, cord 50 is generally long enough for a practitioner to easily find ring 52 when desired.

While shaft 164 may have any desired shape, in an exemplary embodiment, shaft 164 may include a generally tubular base portion coupled to a conical front portion 168, as shown. Additionally, shaft 164 may be manufactured to any desired size or dimension, however, in an exemplary embodiment, the length of shaft 164 (from the end of the base to the tip 166) may fall in the range of 0.25 of an inch to 1.5 inches and the outer diameter of shaft 164 may fall in the range of 0.005 to 0.350 of an inch. The remaining fastener components, as shown in FIGS. 10B-10D, may be sized to be generally proportional to the overall length and width of shaft 164. Shaft 164 may also comprise an integrally formed structure made of any material suitable for patient implantation, such as a plastic.

Referring to FIG. 10B, the remaining fastener components are shown. A shaft 174 may be coupled at one end to the interior and near the tip 166 of shaft 164. An interior wall 172 including an aperture provides further support to shaft 174. Shaft 174 may include a pair of detents 176 and 178 for holding shaft 174 in a retracted position (detent 176) or a deployed position (detent 178).

Referring to FIGS. 10B-10D, a sequence of side elevation views demonstrate a manner of deploying the retractable barb formed by the leading end of shaft 164. FIG. 10B depicts the retractable barb in an initial retracted position. From this condition, a practitioner would pull on ring 52 and cord 50 to pull shaft 174 in a direction away from tip 166. Use of tool 202, as previously discussed, may be useful to hold fastener 162 in place during the operation to deploy the retractable barb. Pulling shaft 174 in a direction away from tip 166 causes the living hinges formed by thinned portions 170 to deform, as shown in FIGS. 10C and 10D. Once the translation is complete, the retractable barb is formed (or deployed) by the end of shaft 164, as shown in FIG. 10D.

Typically, the practitioner will have inserted fastener 162 into the patient with a tool (not shown) that may be applied around the edge of the base. During the insertion of fastener 162 into the patient, the retractable barb is typically left in the retracted or stowed position, as shown in FIG. 10B, to limit patient trauma during fastener insertion. Once inserted, the retractable barb may be deployed, as described above. Assuming the practitioner is not satisfied with the placement of fastener 162 or its related medical structure (not shown, but analogous to any such structure shown in any system embodiment described herein), the practitioner may remove the system (i.e., the medical structure and its related barb or barbs) without damage thereto or to the patient and then reattach the system in the desired location.

To remove the system, the practitioner may employ a second cord 50 and ring 52. The first cord 50 and ring 25 may be attached, as shown in FIG. 10B, for deploying the retractable barb. The second cord 50 and ring 25 (not shown) may be attached to shaft 164 for holding fastener 162 in place during the stowing operation of the retractable barb, as hereafter described. The practitioner may locate the second ring 25, as previously discussed, and use it to apply a counterforce to shaft 164, holding it in place during the stowing operation of the retractable barb. A tool (not shown) may be inserted in through the opening in the base of shaft 164 to apply force against shaft 174. This will move shaft 174 toward the tip 166 of shaft 164 and return shaft 164 to its initial configuration, as shown in FIG. 10B, in which the barb is retracted. Once the barb is retracted, the practitioner may use the second ring 25 to withdraw the fastener 162, while minimizing patient trauma with retracted barb. Assuming other fasteners 162 are included with the subject system, the practitioner may similarly remove them and the related medical structure, intact and undamaged, for reuse.

Regarding FIG. 11A, a side elevation view is shown of an embodiment of a fastener 180 for use in a system for providing medical treatment, in accordance with systems and methods consistent with the present invention. Fastener 180 may include a shaft 182 having a conical front portion 186 and a tip 184 of a size and shape to minimize resistance from insertion of fastener 180 into a patient. A cord 50 and a ring 52 may be coupled to fastener 180 to facilitate removal of fastener 180, if and when desired. The three dots shown in-line with cord 50 indicate that cord 50 may have any desired length, however, cord 50 is generally long enough for a practitioner to easily find ring 52 for removal of fastener 180, if desired.

While shaft 182 may have any desired shape, in an exemplary embodiment, shaft 182 may include a generally tubular base portion coupled to a conical front portion 186, as shown. Additionally, shaft 182 may be manufactured to any desired size or dimension, however, in an exemplary embodiment, the length of shaft 182 (from the end of the base to the tip 184) may fall in the range of 0.25 of an inch to 1.5 inches and the outer diameter of shaft 182 may fall in the range of 0.005 to 0.350 of an inch. The remaining fastener components, as shown in FIGS. 11B-11D, may be sized to be generally proportional to the overall length and width of shaft 182. Shaft 182 may also comprise an integrally formed structure made of any material suitable for patient implantation, such as a plastic. The base of shaft 182 may be sealed, except for an aperture.

Referring to FIG. 11B, the remaining fastener components are shown. A hollow shaft 188 passes through the aperture in the base of shaft 182. The opposing end of hollow shaft 188 may pass through an aperture in the tip 184 of shaft 182. An inflatable body 190 may extend around the opening in the leading end of shaft 188 and be sealed such that fluid flow from the opening in the leading end of shaft 188 inflates inflatable body 190. The opening in the leading end of shaft 188 need not extend outside of shaft 182, but may instead be coplanar with the aperture in the tip 184 of shaft 182 or reside beneath the aperture in the tip 184 of shaft 182, as long as the inflatable body 190 may be inflated as desired.

Referring to FIGS. 11B-11D, a sequence of side elevation views demonstrate a manner of deploying the retractable barb formed by the inflatable body 190. FIG. 11B depicts the retractable barb in an initial retracted position. From this condition, a practitioner would place a tool (not shown) around the aperture in the hollow shaft 188 extending outside of the base of shaft 182. This tool may selectively force fluid into inflatable body 190, causing deployment of the retractable barb, as shown in FIGS. 11C and 11D. Once inflation is complete, the retractable barb is formed (or deployed) by inflatable body 190, as shown in FIG. 11D. The ring 52 and cord 50 may be employed to counterbalance any force applied by the inflating tool, which may cause the fastener 182 to move in an undesired manner. Inflation fluids may comprise any desired gas or liquid. In an exemplary embodiment, the inflation fluid comprises a gas, such as compressed air. Once a desired placement of fastener 180 is reached, a permanent fluid may be utilized (following drainage of the initial inflation fluid), such as a curable polymer, e.g., a curable polymer liquid, gel, foam, epoxy or the like, or a two-part curable system, e.g., a polyurethane, a collagen, a polyethylene glycol or the like.

Typically, the practitioner will have inserted fastener 180 into the patient with a tool (not shown) that may make contact with the base of shaft 182. During the insertion of fastener 180 into the patient, the retractable barb is typically left in the retracted or stowed position, as shown in FIG. 11B, to limit patient trauma during fastener insertion. Once inserted, the retractable barb may be deployed, as described above. Assuming the practitioner is not satisfied with the placement of fastener 180 or its related medical structure (not shown, but analogous to any such structure shown in any system embodiment described herein), the practitioner may remove the system (i.e., the medical structure and its related barb or barbs) without damage thereto or to the patient and then reattach the system in the desired location.

To remove the system, the practitioner may use the inflation tool to deflate inflatable body 190 (or simply drain the inflation fluid without use of the inflation tool). Once the inflation fluid has been drained, the retractable barb is returned to its initial configuration, as shown in FIG. 11B. Once the retractable barb is stowed, the practitioner may use ring 52 to withdraw the fastener 180, while minimizing patient trauma with retracted barb. Assuming other fasteners 180 are included with the subject system, the practitioner may similarly remove them and the related medical structure, intact and undamaged, for reuse.

Other embodiments of the invention will be apparent to those skilled in the art from consideration of the specification and practice of the invention disclosed herein.

For example, embodiments of the present invention may include a structure for attachment to a patient, the structure being coupled to one or more fasteners, wherein each fastener includes a source for providing variable friction (or holding force). A retractable barb provides variable friction (or holding force), however, there may be other fasteners that provide such variable friction (or holding force).

For example, one could envision a fastener including a controllable inflation source having an expandable stent-like device around it. Once the fastener was inserted to a desired location in a patient, the practitioner may inflate the controllable inflation source, expanding the stent-like device and increasing local friction. Once the stent-like device was expanded, the practitioner may deflate the controllable inflation source and remove it, leaving an expanded stent-like device providing increased local friction (or holding force). This exemplary system is not reversible, i.e., once the stent-like device is expanded, it remains so, meaning device retraction may produce patient trauma.

Thus, more generally, embodiments of the present invention may include any structure for attachment to a patient, wherein the structure is coupled to one or more fasteners that any source for providing variable friction (or holding force) once implanted in the patient, whether the source is reversible or not.

Further supplementing the disclosure herein is FIGS. 15A-15F below, which show an embodiment of a retractable barb with enhanced anchoring. This embodiment of the present invention may be incorporated with any embodiment disclosed herein or any embodiment disclosed in any related application.

FIGS. 15A-15F depict another embodiment of the present invention providing a retractable barb having enhanced anchoring capability. Referring to FIG. 15A, an embodiment of such a retractable barb (or more simply the "barb") 1500 is shown. Barb 1500 may include a pair of retractable arms 1502 and 1504 that may be coupled to a base member 1506. In one embodiment of the present invention, the retractable arms 1502 and 1504 as well as the base member 1506 may be fabricated using a plastic-type material; however, those skilled in the art will understand that any suitable material may be employed, as desired. The retractable arms 1502 and 1504 may be coupled together at an upper apex, as shown in FIG. 15A, and may be coupled to base member 1506 at lower ends of arms 1502 and 1504. Base member 1506 may include an aperture (not shown) to permit a tool tip 1508 to selectively penetrate the aperture and engage on an interior lower portion of the apex for the barb 1500. This engagement point for tool tip 1508 may include an enhanced indentation to receive tool tip 1508. Such an enhanced indentation may more easily facilitate guiding tool tip 1508 to the position shown in FIG. 15A.

Referring to FIGS. 15A and 15B, one can see that the retractable barb 1500 is shown in an expanded profile in FIG. 15A and in a relaxed state in FIG. 15B. The expanded profile of barb 1500, as shown in FIG. 15A, provides a more vertically sleek configuration for insertion of barb 1500 into the tissue of a patient (i.e., vertically expanded and horizontally contracted, providing reduced cross-section and resistance during insertion). The relaxed state of barb 1500, as shown in FIG. 15B, shows a shorter configuration vertically and an expanded horizontal configuration of retractable arms 1502 and 1504. The relaxed state of barb 1500 may comprise the position of barb 1500 when not acted upon by tool tip 1508 and tool 1510, as shown in FIG. 15D. The relaxed state of barb 1500 provides an improved wide aspect ratio for anchoring to multiple tissue surfaces.

FIG. 15C shows a side view of barb 1500, and in particular, a side view of retractable arm 1502. In this view, one can see the curved concave portions 1502A and 1502B (similar concave portions may be found in retractable arm 1504), which may give an improved simulated cutting-edge for insertion of barb 1500 into the tissue of the patient. The curved concave portions 1502A and 1502B, providing the improved simulated cutting-edge (or more simply, the cutting-edge) for creating an incision to insert barb 1500 into the tissue of the patient, may take alternative forms for facilitating such incision and insertion of barb 1500. More generally, the upper surfaces of retractable arms 1502 and 1504 may, instead of having curved concave portions 1502A and 1502B, include any shape deemed suitable for facilitating such incision and insertion of barb 1500. For example, one could have linear, as opposed to curved, cutouts in retractable arms 1502 and 1504, although any desired shape may be formed into the upper surfaces of retractable arms 1502 and 1504 to facilitate such incision and insertion of barb 1500.

Referring to FIG. 15D, tool 1510 is shown engaged with barb 1500. Tool 1510 may include fingers 1512 and tool tip 1508. In one embodiment of tool 1510, fingers 1512 may be locked in an open position (for moving tool 1510 into position shown in FIG. 15D) such that once tool tip 1508 is inserted into the aperture (not shown) in base member 1506, fingers 1512 may extend to a position slightly above the upper surface of base member 1506. Once in this position, a release may be actuated by a user to unlock fingers 1512, allowing them to move into position (by spring or other motive force) and engage against the upper surface of base member 1506, as shown in FIG. 15D. In this position, a user may pull back on tool 1510, causing retractable arms 1502 and 1504 to expand from an inserting configuration, as shown in FIG. 15 A, to the relaxed state of barb 1500, as shown in FIG. 15B. In this manner, a user can first insert barb 1500 to a desired position, and then withdraw tool 1510 to expand barb 1500 to the relaxed state in which barb 1500 is configured for enhanced anchoring to the tissue of the patient.

Referring to FIG. 15F, base member 1506 is shown to include a pair of apertures 1514. In one embodiment of the present invention, one such aperture may be used to accommodate a suture that may be employed for any desired purpose, such as providing a means to fasten barb 1500 or withdraw barb 1500 (to facilitate withdrawal of barb 1500, a user may push up on tool tip 1508 to narrow the horizontal aspect of barb 1500, as depicted in FIG. 15 A, thereby reducing friction and the amount of force required to withdraw barb 1500, whether such force be provided by pulling on a suture or otherwise). Another such aperture may be used to couple barb 1500 to a support structure 1516, such as a mesh strip. In another embodiment, such a support structure 1516 may be directly coupled to base member 1506, in which case the apertures shown may or may not be used. The support structure 1516, such as a mesh strip coupled directly to base member 1506, may itself have attached thereto one or more sutures that may be employed for any desired purpose, such as providing a means to withdraw barb 1500 or fasten barb 1500. As shown in FIG. 15F, the relaxed state of barb 1500 provides an area between retractable arms 1502 and 1504 and base member 1506 in which tissue may grow, providing enhanced anchoring of retractable barb 1500. In addition, the expanded profile of retractable barb 1500, as shown in FIG. 15B, may also provide enhanced anchoring of barb 1500.

Similarly supplementing the disclosure herein is: (1) FIGS. 16A-16B which show an embodiment of an improved sling, an embodiment of an improved retractable anchor with enhanced anchoring and an embodiment of an improved tool for use with the sling and anchor embodiments herein, (2) FIGS. 17A-17B which show an embodiment of an improved anchoring mechanism, including a tool for employing same, and (3) FIGS. 18A-18C which show embodiments of the improved sling, anchoring mechanism and tool of FIGS. 16A-16B and FIGS. 17A-17B. As before, these embodiments of the present invention may be incorporated with any embodiment disclosed herein or any embodiment disclosed in any related application.

Figure 16A:
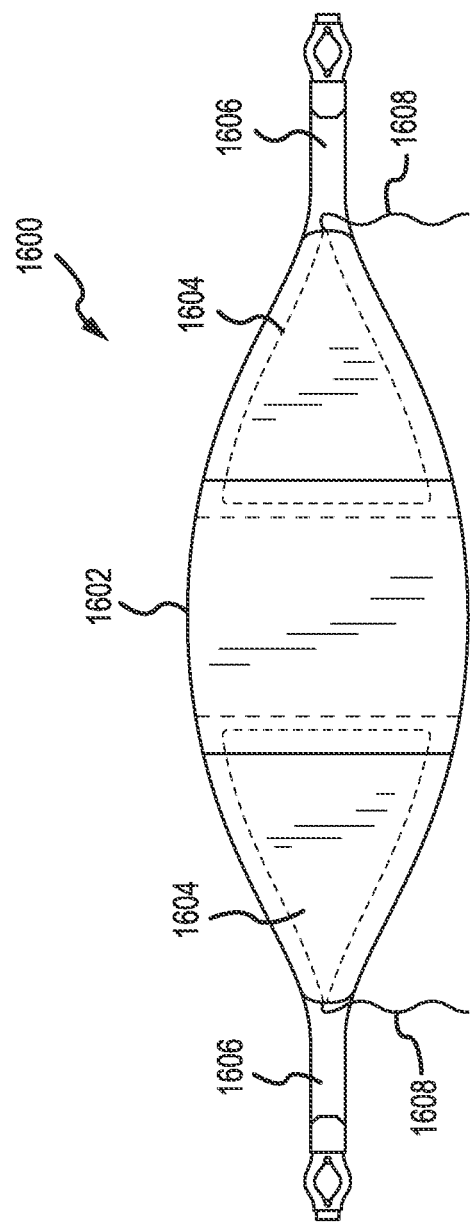

Referring to FIG. 16A, an embodiment of an improved sling 1600 is shown. In a central portion of sling 1600, a region 1602 may be included comprising a biocompatible elastomeric material, such as a silicon-based material, a rubber-like material or a stretchable biomedical-grade polymer. This material may comprise any biocompatible elastomeric material that may be stretched. On either side of central region 1602 may be located a pair of sections 1604, each of which may comprise a conventional mesh material. Coupled to the outer edges of the mesh material 1604 may be sections 1606, which may similarly be comprised of a biocompatible elastomeric material. The very ends of sling 1600 may include a region including an aperture for connection to an anchoring mechanism (not shown).

In one embodiment of the present invention, sling 1600 may include the region 1602 comprising a biocompatible elastomeric material, while the remainder of sling 1600 may comprise a conventional mesh material 1604. In another embodiment of the present invention, sling 1600 may include the pair of sections 1606, each comprising a biocompatible elastomeric material, while the remainder of sling 1600 comprises a conventional mesh material 1604. In yet another embodiment of the present invention, sling 1600 may include only one of the pair of sections 1606, this one of the pair of sections 1606 comprising a biocompatible elastomeric material, while the remainder of sling 1600 comprises a conventional mesh material 1604. In still another embodiment of the present invention and as depicted in FIG. 16 A, sling 1600 may include the region 1602 and the pair of sections 1606, each comprising a biocompatible elastomeric material, while the remainder of sling 1600 comprises a conventional mesh material 1604. More generally, sling 1600 may include both a first portion comprising a biocompatible elastomeric material and a second portion comprising a conventional mesh material, while this embodiment and any of the foregoing embodiments may include one or more sutures 1608, as depicted in FIG. 16A or as otherwise desirable.

The various materials comprising sling 1600 may be integrally formed into a unitary sling. Sections 1602 and/or 1606 comprising a biocompatible elastomeric material may be omitted, in which case a conventional mesh material may be substituted therefor. Assuming a centrally located section 1602 of biocompatible elastomeric material is employed, this material may include an aperture running through it, as shown in FIG. 16A, to accommodate one or more sutures 1608. The sutures 1608 may comprise any conventional suture. The suture 1608 may, as shown in FIG. 16A, be woven through the apertures (not shown) in mesh sections 1604 of sling 1600. The ends of sutures 1608 may penetrate sections 1606, if employed, with the ends of the sutures 1608 extending outside of sling 1600 for access and use by the surgeon or other medical professional.

Use of a biocompatible elastomeric material, whether in sections 1606 and/or 1602 or otherwise, as desired, affords an element of flexibility to sling 1600 heretofore unavailable. The surgeon or other medical professional may as a result pull on the sutures 1608 located on either side of sling 1600 to stretch the sling 1600 along its longitudinal axis (the lengthwise axis, as shown in FIG. 16A). As such, once the sling 1600 is attached to a patient using anchors (not shown) coupled on either end of sling 1600, the surgeon or other medical professional may pull on one or both sutures 1608 to stretch the sling 1600, affording great compression against the patient area being supported by sling 1600. Moreover, unlike current slings which are static, the use of one or more biocompatible elastomeric material sections 1606 and/or 1602 or otherwise, as desired, in sling 1600 will allow support compensation in the sling 1600 to accommodate for the changes that occur in one's activity level and body habitus over the life of the patient. The biocompatible elastomeric material sections 1606 and/or 1602 will maintain the necessary urethral co-aptation, compression and elevation necessary to obviate the incontinence that may be likely to occur with the aforementioned changes in activity and body habitus throughout the patient's life and thus maintain continence. In other words, in comparison to the current static slings in the art, embodiments of the present invention comprise a dynamic sling 1600 which has the potential to maintain efficacy over time.

Referring to FIG. 16B, sling 1600 of FIG. 16A is shown in perspective view attached to a tool 1614 for employing sling 1600. Attached to tool 1614 is an anchor 1610 coupled on both ends of sling 1600. Each anchor 1610 penetrates their respective aperture located on the ends of sling 1600, as shown in FIG. 16A. Also shown in FIG. 16B is an extension member 1612 coupled to each end of sling 1600. Extension member 1612 may be utilized to help guide tool 1614 into a meeting engagement with anchor 1610, as shown in FIG. 17B.

Figure 17A:
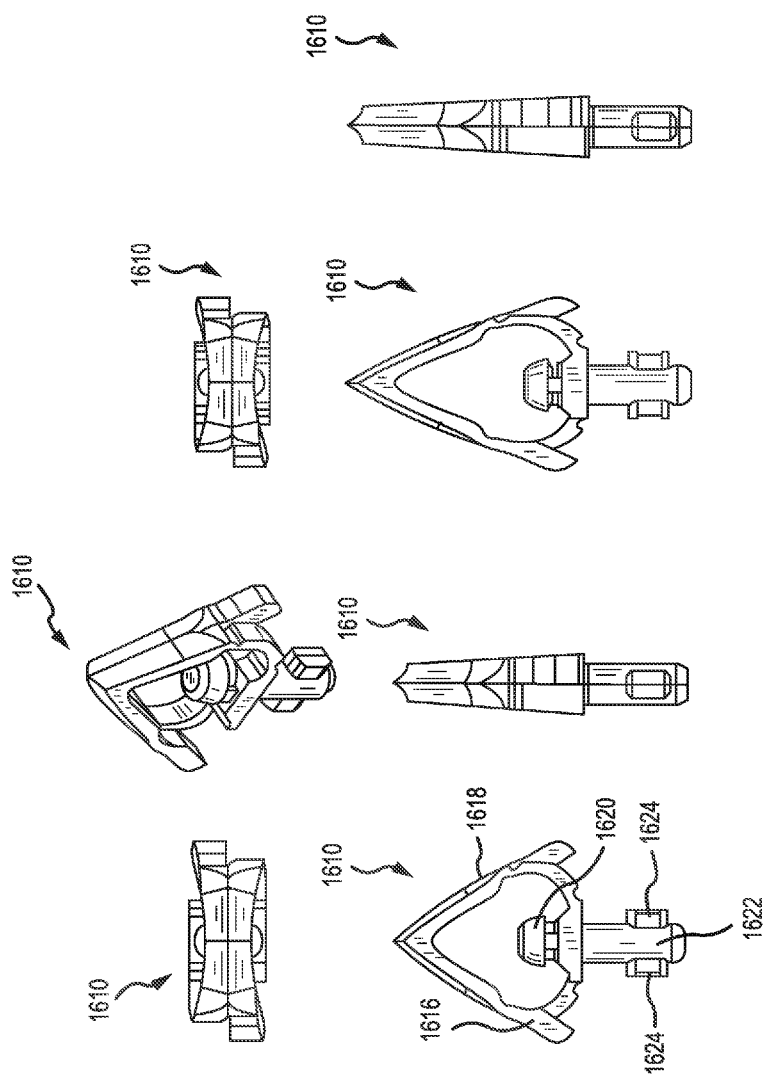

Referring to FIG. 17A, an embodiment of an improved anchoring mechanism 1610 is shown. For the sake of clarity, the terms "anchor," "anchoring mechanism" or the like are intended herein to correspond to the terms "barb," "retractable barb" or the like. In other words, whether the term being used herein is a barb, a retractable barb, an anchor, a retractable anchor, or the like, the intent is that these terms describe a structure for connecting to the tissue or other part of a patient.

FIG. 17A depicts various views of an improved embodiment of anchor 1610. The retractable anchor 1610 shown in FIG. 17A is similar to the retractable barb (or retractable anchor) shown in FIGS. 15A-F above. Each retractable anchor (or retractable barb) includes a pair of arms such as moveable arms 1616 and 1618 shown in FIG. 17A. The changes to the embodiment of the retractable anchor 1610 shown in FIG. 17A, as compared to the retractable anchor shown in FIGS. 15A-F, are as follows. The base member connecting moveable arms 1616 and 1618 includes a flared cap 1620 coupled to a keying mechanism located above and coupled to a shaft 1622, which includes a pair of locking tabs 1624. The keying mechanism located beneath flared cap 1620 may be used in conjunction with the aperture located on either end of sling 1600, as shown in FIG. 16A, to fix the relative position of sling 1600 as compared to anchor 1610 (i.e., the key mechanism fixes the lengthwise axis of sling 1600 relative to anchor 1610). The flared cap 1620 may hold sling 1600 against the base member of anchor 1610. Shaft 1622 may include a vertical aperture to accept a pin such that the pin can engage with the upper inner apex located between moveable arms 1616 and 1618 for adjustment of moveable arms 1616 and 1618. As was the case for the embodiment shown in FIGS. 15A-F, the embodiment shown here may similarly include one or more sutures for fastening or facilitating the removal of an anchor 1610 from a patient's tissue, and such sutures may be attached through one or more apertures (not shown) in base member of anchor 1610, although such sutures may, if used, be attached in any one of a number of different manners.

Regarding flared cap 1620, in one embodiment flared cap 1620 may be fixedly attached to the base member, so that an aperture located at an end of sling 1600 may be fit over and slid down and below flared cap 1620, permitting the aperture to reach proper alignment with the key located beneath flared cap 1620. In an alternative embodiment, flared cap 1620 may be removably attached to the base member, so that the aperture located at an end of sling 1600 may be put into proper alignment with the key located beneath flared cap 1620, following the detachment of flared cap 1620, the flared cap 1620 then being reattached once the sling 1600 is put into proper alignment with the key. Sling 1600 may be manufactured to have each end pre-attached to an anchor 1610, so that the sling 1600 is ready for use upon delivery. Alternatively, sling 1600 may be initially provided without having been attached to anchors 1610, leaving the task of attachment of the sling 1600 to each anchor 1610 (as discussed above) for an end-user.

Referring to FIG. 17B, the pin 1626 of tool 1614 is shown. Pin 1626 may include one or more flattened (or otherwise keyed) regions along its shaft corresponding to matching regions within the aperture penetrating the shaft 1622 for orientation while inserting pin 1626 through shaft 1622. A tube 1628 may be located around pin 1626. Tube 1628 may include cutout regions for accepting tabs 1624 extending from shaft 1622. The left-most and center views shown in FIG. 17B show the tabs 1624 in an unlocked position (i.e., tabs 1624 are not yet rotated to fit inside the cutout in tube 1628). The right-most view shown in FIG. 17B shows tab 1624 located in the cutout in tube 1628. This is the locked position of tool 1614, permitting the extension of pin 1626 for insertion of anchor 1610 into a patient. Tool 1614 also may include a stop 1630 for limiting (by abutment with a patient) the insertion of anchor 1610 into the patient. A notch may be located on one or both sides of the stop 1630 for receiving guide member 1612. This arrangement helps guide tool 1614 into proper alignment with anchor 1610. Guide members 1612 may be removed (e.g., by severing) after tool engagement with anchor 1610 or following attachment of sling 1600 or whenever else the surgeon deems desirable.

Figure 18A:
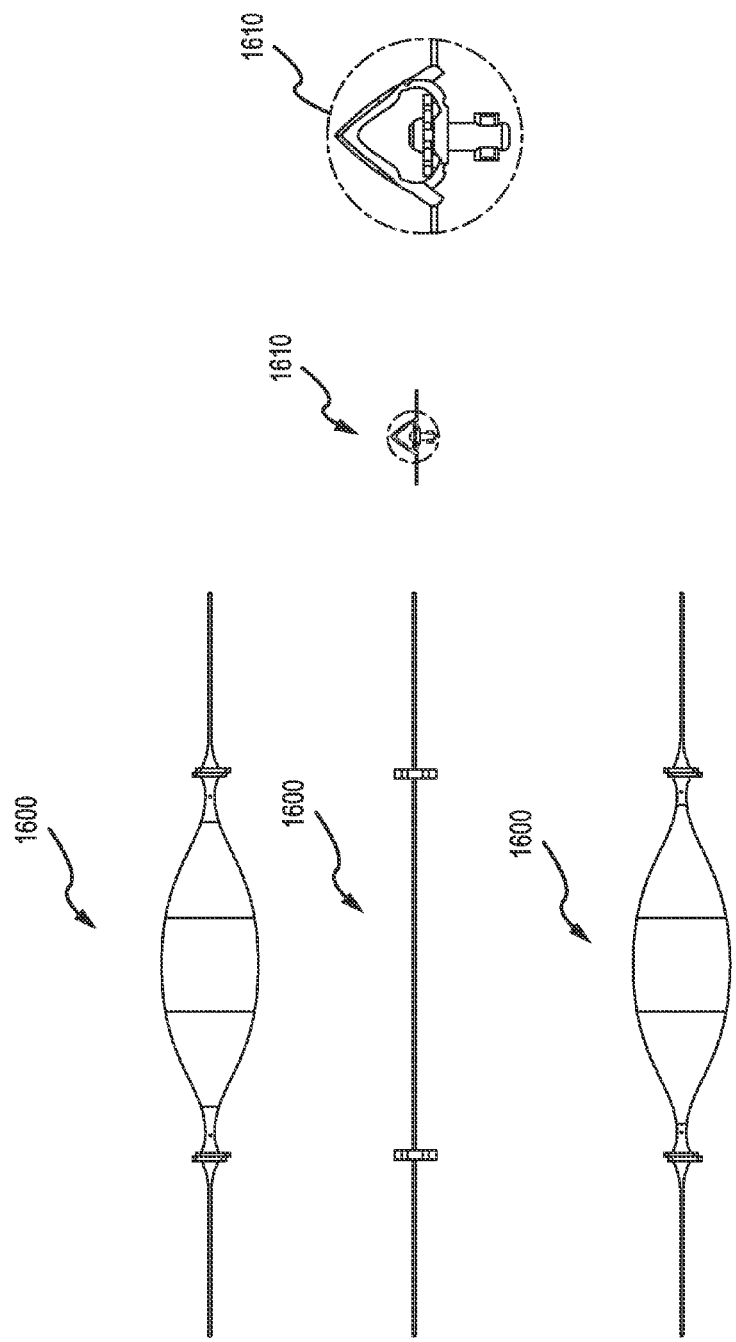
FIGS. 18A-18C show embodiments of the improved sling, anchoring mechanism and tool of FIGS. 16A-16B and FIGS. 17A-17B, in accordance with systems and methods consistent with the present invention.
Figure 18B:
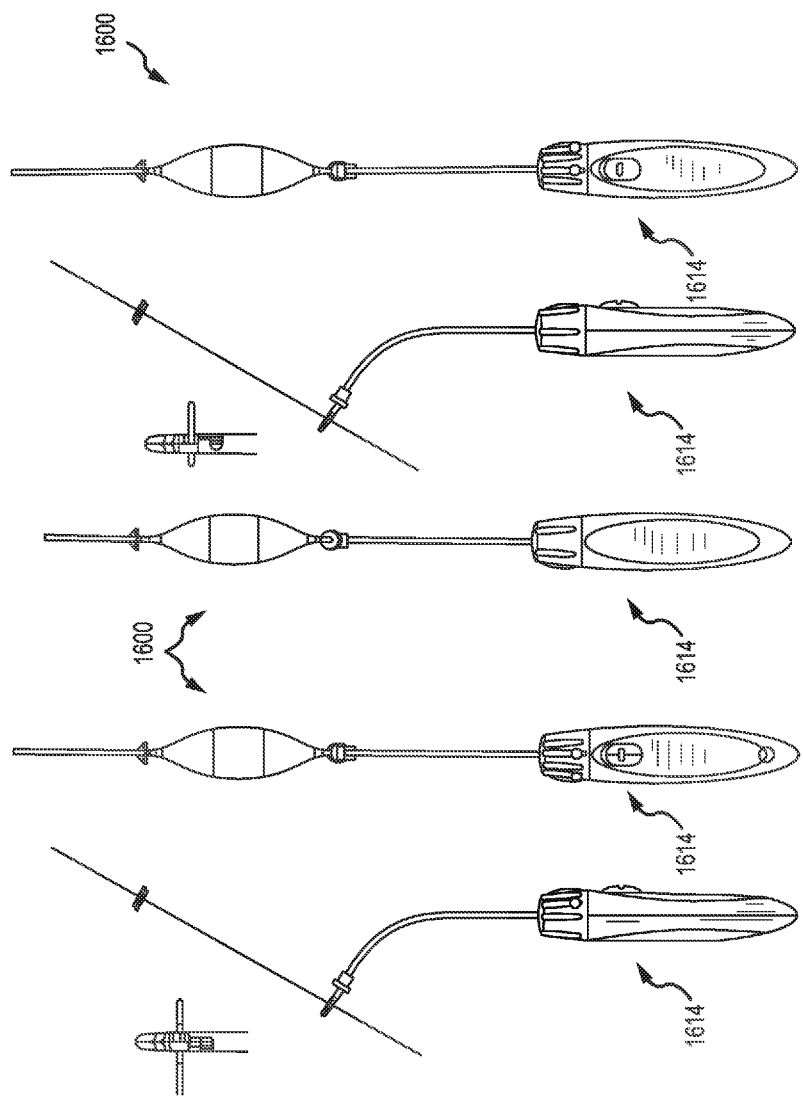
Figure 18C:
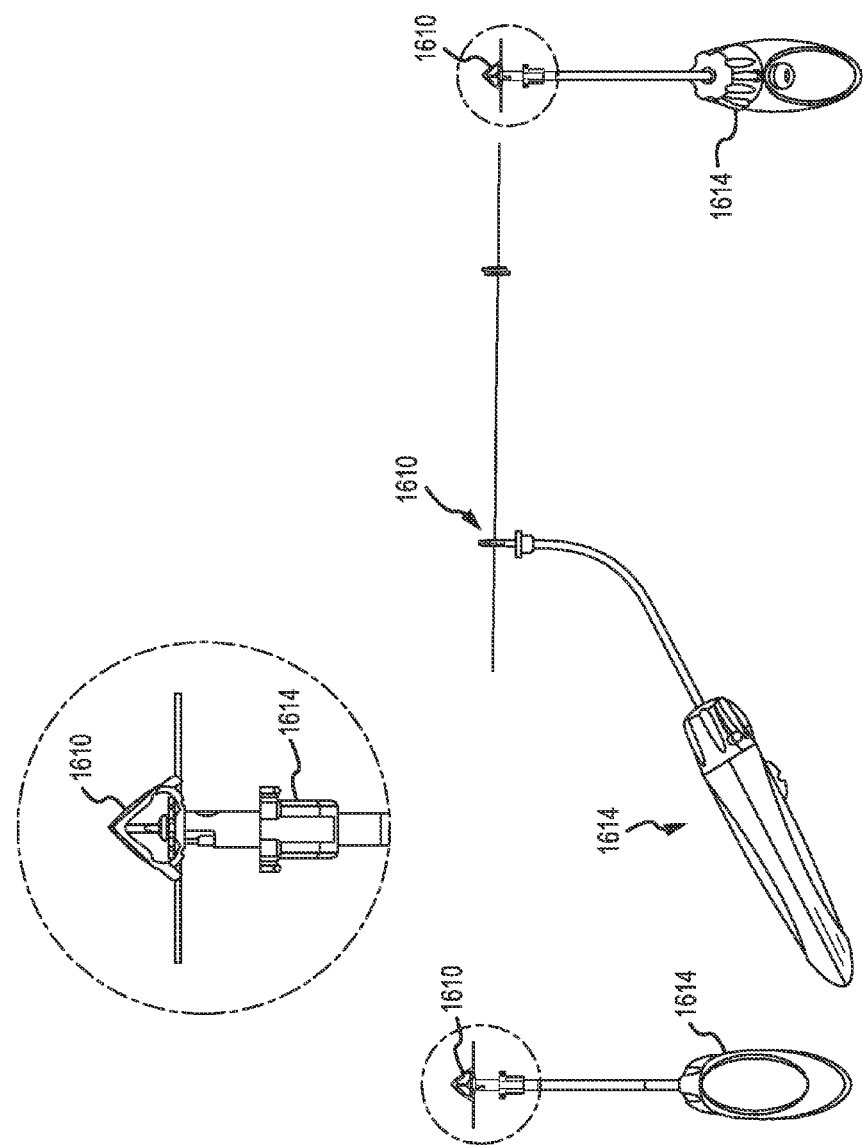

FIGS. 18A-18C show various views of sling 1600, anchor 1610, and tool 1614, as described above with reference with FIGS. 16A, 16B, 17A, and 17B. As shown in FIG. 18B, tool 1614 includes a knob to selectively rotate to lock or unlock tool 1614 with an anchor 1610. Specifically, actuation of the knob to lock rotates tube 1628 to a locked position, as shown in the right-most view in FIG. 17B, while actuation of the knob to unlock rotates to 1628 to an unlocked position, as shown in the center and left-most views in FIG. 17B. Once in a locked position, a user may actuate the pin driver (best viewed in the right-most view of FIG. 18B). The pin driver may be pushed up to drive up pin 1626 only when the tool's knob has been actuated to the locked position. Driving up pin 1626 may be used to create an incision in the patient through the leading edges of anchor 1610 and insert the anchor 1610 to a desired position. Once in the desired position, the pin 1626 may be withdrawn (again using the pin driver on tool 1614) to permit expansion of the anchor 1610 for improved holding capacity. Additionally, the pin driver on tool 1614 may be used to drive pin 1626 against the upper internal apex of anchor 1610 to elongate anchor 1610 and facilitate the withdrawal of same for relocation, if desired, such withdrawal being made using the help of sutures which may be attached.

Figure 19:
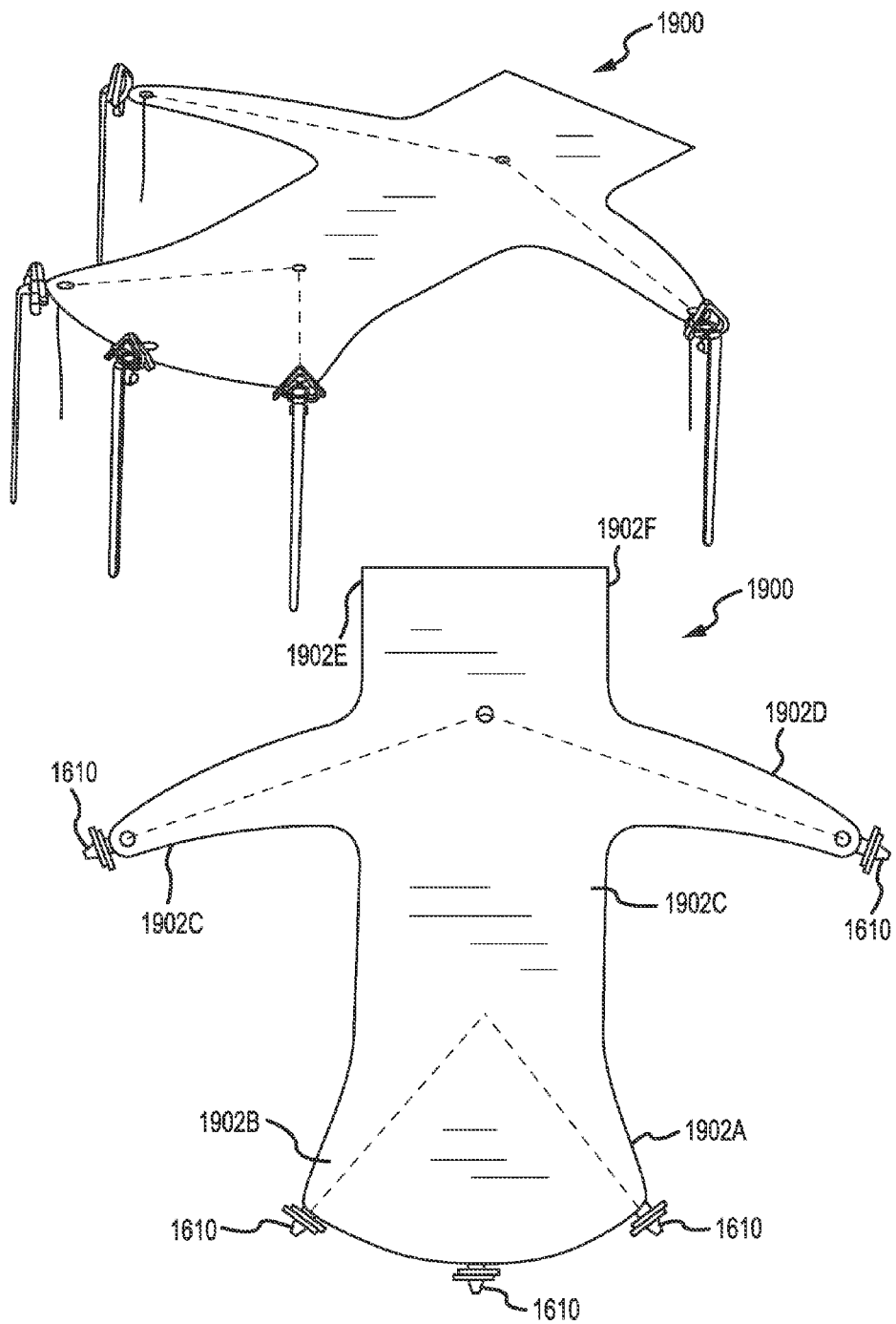
FIGS. 19 and 20 show embodiments of slings, in accordance with systems and methods consistent with the present invention.
Figure 20:
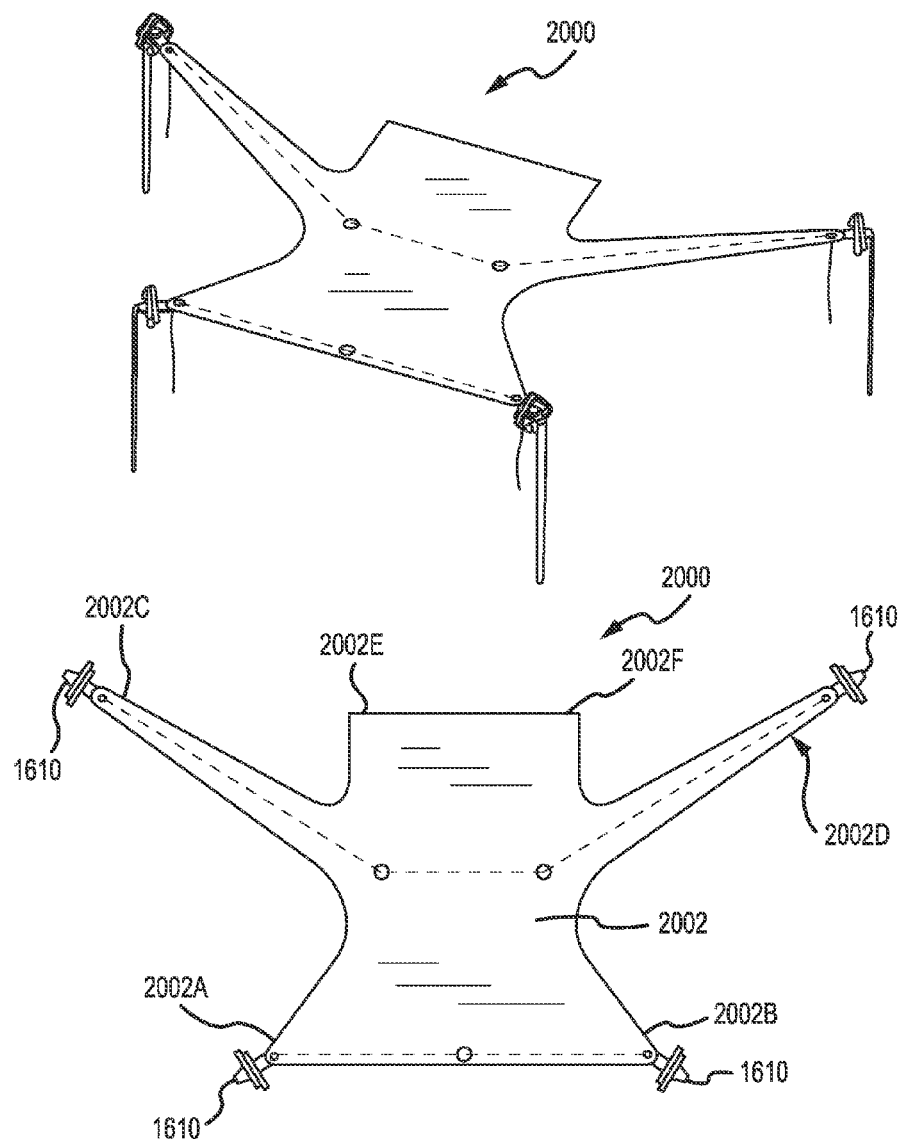

Similarly supplementing the disclosure herein is FIGS. 19 and 20, which shows additional sling embodiments. As before, these embodiments of the present invention may be incorporated with any embodiment disclosed herein or any embodiment disclosed in any related application.

The sling embodiments depicted in FIGS. 19 and 20 may include one or more adjustment lanyards (such as sutures or any other line that may be used in a medical procedure) integrated with their respective slings. Use of such adjustment lanyards gives the surgeon or other medical professional the opportunity to adjust the tension across the sling (typically once the sling has been anchored to the patient), thereby affecting the strength of support provided by the sling to the relevant portion of the patient. The adjustment lanyards may be woven through apertures found in the mesh (such weaving may be from aperture to adjacent aperture or skip one or more apertures at a time) forming the sling or integrated with the mesh in any other desired manner. Moreover, whether one adjustment lanyard or a plurality of adjustment lanyards are employed with the sling, they may be integrated anywhere on the sling, whether the adjustment lanyards be integrated around perimeter portions of the sling or any area inside the perimeter of the sling or any combination of the foregoing.

The shape of the sling embodiment in FIG. 19, as well as the suture placement, may be desirably employed in a rectocele procedure, while the shape of the sling embodiment in FIG. 20 and suture placement may be desirably employed in a cystocele procedure. More generally, one or more adjustment lanyards, as shown in FIGS. 19 and 20 and described herein, may be employed with any sling embodiment (or indeed any mesh or similar material, whether used as a sling or not) to provide the capability to adjust the tension across the support material and thereby adjust the level of support provided to the affected patient area.

Referring to the sling embodiment of FIG. 19, sling 1900 may be comprised of a conventional mesh material. However, as with other sling embodiments disclosed herein, sling 1900 may utilize, in addition to a conventional mesh material, one or more regions (not shown) comprising a biocompatible elastomeric material, such as a silicon-based material, a rubber-like material or a stretchable biomedical-grade polymer. This material may comprise any biocompatible elastomeric material that may be stretched.

Sling 1900 may include a generally rectangular portion 1902 having at one end thereof a pair of squared corners 1902E and 1902F ("the squared corners end") and at an opposing end thereof a pair of rounded corners 1902A and 1902B ("the rounded corners end"). The rounded corners end of sling 1900 may include a pair of sections deviating and expanding outwardly from the generally rectangular shape of sling 1900. Specifically, the deviations from the generally rectangular shape of sling 1900 may comprise a pair of generally triangular-shaped sections, each of which may terminate at a respective rounded corner 1902A and 1902B. Between rounded corners 1902A and 1902B may be a curved perimeter portion. Finally, located nearer the squared corners end of sling 1900 than the rounded corners end of sling 1900 may be a pair of arms 1902C and 1902D. Located near the end of each arm 1902C and 1902D may be an anchor 1610. Similarly, located at each rounded corner 1902A and 1902B may be an anchor 1610 and located on the curved perimeter portion between rounded corners 1902A and 1902B may be an anchor 1610.

Referring to the sling embodiment of FIG. 20, sling 2000 may be comprised of a conventional mesh material. However, as with other sling embodiments disclosed herein, sling 2000 may utilize, in addition to a conventional mesh material, one or more regions (not shown) comprising a biocompatible elastomeric material, such as a silicon-based material, a rubber-like material or a stretchable biomedical-grade polymer. This material may comprise any biocompatible elastomeric material that may be stretched.

Sling 2000 may include a generally rectangular portion 2002 having at one end thereof a pair of squared corners 2002E and 2002F ("the squared corners end") and at an opposing end thereof a pair of rounded corners 2002A and 2002B ("the rounded corners end"). The rounded corners end of sling 2000 may include a pair of sections deviating and expanding outwardly from the generally rectangular shape of sling 2000. Specifically, the deviations from the generally rectangular shape of sling 2000 may comprise a pair of generally triangular-shaped sections, each of which may terminate at a respective rounded corner 2002A and 2002B. Located nearer the squared corners end of sling 2000 than the rounded corners end of sling 2000 may be a pair of arms 2002C and 2002D. Located near the end of each arm 2002C and 2002D may be an anchor 1610. Similarly, located at each rounded corner 2002A and 2002B may be an anchor 1610.

The geometrical configurations of the different slings shown herein are such that they may recreate and facilitate the normal anatomical support that is necessary to resolve the problem for which they are being utilized. The differences between the geometrical configurations of the slings for the cystocele procedure (e.g., for bladder prolapse/hernia) and the rectocele procedure (e.g., for rectal prolapse/hernia) may depend upon the anatomical repair one is attempting to achieve. The geometrical configurations for both the male and the female slings utilized in the treatment of SUI may facilitate the need to increase and maintain compression and elevation at the bulbous urethra for the male and at the bladder neck (urethral-vesical junction) for the female in order to facilitate the increased resistance necessary to overcome the SUI.

It is intended that the specification and examples be considered as exemplary only, with a true scope and spirit of the invention being indicated by the claims, as yet to be filed in one or more related applications.

What is claimed is:

1. A system for providing medical treatment to a patient, the system comprising:
   an implantable structure for attachment to the patient, the structure having a first end and a second, opposing end;
   a first aperture located near the first end of the structure, the first aperture configured to receive a first key for insertion of a first retractable barb and for establishing a desired alignment of the structure with respect to the first retractable barb;
   a second aperture located near the second end of the structure, the second aperture configured to receive a second key for insertion of a second retractable barb and for establishing a desired alignment of the structure with respect to the second retractable barb;
   wherein the first retractable barb and the second retractable barb each comprise:
      a pair of movable arms, each movable arm having a first and a second end, the first ends of the pair of movable arms being coupled together;
      a base member having a first end and a second end, the first end and the second end of the base member each being coupled in proximity to the second end of a respective one of the pair of movable arms; and
      wherein the pair of movable arms and the base member form a triangular structure having an outer surface and an inner surface, the inner surface forming an aperture between the pair of movable arms and the base member for tissue growth;
   a stem coupled to the base member, said stem including an aperture running lengthwise through the stem to permit insertion of a tool for moving one of the first and the second retractable barbs; and
   a pair of locking tabs coupled to the stem, when moved into a first position the pair of locking tabs permit actuation of the tool to allow for moving one of the first and the second retractable barbs, and when moved into a second position the pair of locking tabs prevent actuation of the tool.

2. The system of claim 1 wherein the structure comprises a mesh material.

3. The system of claim 2 wherein the structure comprises one or more regions including a biocompatible elastomeric material.

4. The system of claim 3 wherein one of the one or more regions comprises a region centered along a longitudinal axis of the structure.

5. The system of claim 4 wherein another of the one or more regions comprises a region near the first end of the structure and yet another of the one or more regions comprises a region near the second end of the structure.

6. The system of claim 3 wherein one of the one or more regions comprises a region near the first end of the structure.

7. The system of claim 6 wherein another of the one or more regions comprises a region near the second end of the structure.

8. The system of claim 3 wherein the biocompatible elastomeric material comprises one or more of a silicon-based material, a rubber-based material and a stretchable biomedical-grade polymer.

9. The system of claim 3 further comprising one or more sutures coupled to the structure.

10. The system of claim 9 wherein the one or more sutures are integrated within the biocompatible elastomeric material and are woven between apertures formed by the mesh material.

11. The system of claim 10 wherein the one or more sutures comprise a pair of sutures, each suture of the pair of sutures being integrated within the biocompatible elastomeric material and woven between the apertures formed by the mesh material to form a triangular pattern.

12. The system of claim 3 wherein the structure has an elliptical shape.

13. The system of claim 1 further comprising one or more sutures coupled to the structure.

14. The system of claim 1 wherein a portion of the outer surface is formed by outer surfaces of the movable arms and wherein portions of the outer surfaces of the movable arms are adapted for creating an incision in the patient.

15. The system of claim 14 wherein the portions of the outer surfaces of the movable arms that are adapted for creating the incision comprise concave-shaped cutouts.

16. The system of claim 1 wherein each retractable barb is configured to be selectively moved between a first configuration in which the triangular structure is shaped to improve capacity for creating an incision and inserting the retractable barb into the patient and a second configuration in which the triangular structure is shaped to improve holding capacity of the retractable barb within the patient.

17. The system of claim 1 further including an alignment structure coupled to the base member for mating engagement and alignment with a respective key in a respective aperture in the structure.

18. The system of claim 1 wherein each retractable barb comprises a plastic material.

19. The system of claim 1 wherein a portion near the second end of each movable arm extends away from the base member to provide prongs for increased holding capacity within patient tissue.

20. The system of claim 1 wherein the aperture within the stem includes an alignment structure to facilitate proper alignment and insertion of the tool through the aperture within the stem.

21. The system of claim 1 further including a pair of alignment members for facilitating proper alignment and insertion of a tool for controlling each retractable barb.

22. A system for providing medical treatment to a patient, the system comprising:
   an implantable structure for attachment to the patient, the structure having a generally rectangular shape and having extending therefrom a plurality of arms, each arm including a proximal end coupled to the generally rectangular shape of the structure and a distal end;
   an aperture located near the distal end of each arm, each aperture configured to receive a key for insertion of a retractable barb and for establishing a desired alignment of the structure with respect to the retractable barb;
   a plurality of apertures located near a perimeter portion of the generally rectangular shape of the structure, each aperture of the plurality of apertures configured to receive a key for insertion of a retractable barb and for establishing a desired alignment of the structure with respect to the retractable barb;
   a retractable barb coupled to each aperture in the structure;
   wherein each retractable barb comprises:
      a pair of movable arms, each movable arm having a first and a second end, the first ends of the pair of movable arms being coupled together;
      a base member having a first end and a second end, the first end and the second end of the base member each being coupled in proximity to the second end of a respective one of the pair of movable arms; and
      wherein the pair of movable arms and the base member form a triangular structure having an outer surface and an inner surface, the inner surface forming an aperture between the pair of movable arms and the base member for tissue growth;
   a stem coupled to the base member, said stem including an aperture running lengthwise through the stem to permit insertion of a tool for moving one of the retractable barbs; and
   a pair of locking tabs coupled to the stem, when moved into a first position the pair of locking tabs permit actuation of the tool to allow for moving one of the retractable barbs, and when moved into a second position the pair of locking tabs prevent actuation of the tool.

23. The system of claim 22 wherein the structure comprises a mesh material.

24. The system of claim 23 wherein the structure comprises one or more regions including a biocompatible elastomeric material.

25. The system of claim 24 wherein the biocompatible elastomeric material comprises one or more of a silicon-based material, a rubber-based material and a stretchable biomedical-grade polymer.

26. The system of claim 24 further comprising one or more sutures coupled to the structure.

27. The system of claim 22 further comprising one or more sutures coupled to the structure.

28. The system of claim 22 wherein a portion of the outer surface is formed by outer surfaces of the movable arms and wherein portions of the outer surfaces of the movable arms are adapted for creating an incision in the patient.

29. The system of claim 28 wherein the portions of the outer surfaces of the movable arms that are adapted for creating the incision comprise concave-shaped cutouts.

30. The system of claim 22 wherein each retractable barb is configured to be selectively moved between a first configuration in which the triangular structure is shaped to improve capacity for creating an incision and inserting the retractable barb into the patient and a second configuration in which the triangular structure is shaped to improve holding capacity of the retractable barb within the patient.

31. The system of claim 22 further including an alignment structure coupled to the base member for mating engagement and alignment with a respective key in a respective aperture in the structure.

32. The system of claim 22 wherein each retractable barb comprises a plastic material.

33. The system of claim 22 wherein a portion near the second end of each movable arm extends away from the base member to provide prongs for increased holding capacity within patient tissue.

34. The system of claim 22 wherein the aperture within the stem includes an alignment structure to facilitate proper alignment and insertion of the tool through the aperture within the stem.

35. A system including a retractable barb for attaching a portion of an implantable medical device to a patient, the retractable barb comprising:
- a pair of movable arms, each movable arm having a first and a second end, the first ends of the pair of movable arms being coupled together;
- a base member having a first end and a second end, the first end and the second end of the base member each being coupled in proximity to the second end of a respective one of the pair of movable arms; and
- wherein the pair of movable arms and the base member form a triangular structure having an outer surface and an inner surface, the inner surface forming an aperture between the pair of movable arms and the base member for tissue growth;

the system further including:
- a stem coupled to the base member, said stem including an aperture running lengthwise through the stem to permit insertion of a tool for moving the retractable barb; and
- a pair of locking tabs coupled to the stem, when moved into a first position the pair of locking tabs permit actuation of the tool for moving the retractable barb, and when moved into a second position the pair of locking tabs prevent actuation of the tool.

36. The system of claim 35 wherein a portion of the outer surface is formed by outer surfaces of the movable arms and wherein portions of the outer surfaces of the movable arms are adapted for creating an incision in the patient.

37. The system of claim 36 wherein the portions of the outer surfaces of the movable arms that are adapted for creating the incision comprise concave-shaped cutouts.

38. The system of claim 35 wherein the retractable barb is configured to be selectively moved between a first configuration in which the triangular structure is shaped to improve capacity for creating an incision and inserting the retractable barb into the patient and a second configuration in which the triangular structure is shaped to improve holding capacity of the retractable barb within the patient.

39. The system of claim 35 further including an alignment structure coupled to the base member for mating engagement and alignment with a key in an aperture in the medical device.

40. The system of claim 35 wherein the retractable barb comprises a plastic material.

41. The system of claim 35 wherein a portion near the second end of each movable arm extends away from the base member to provide prongs for increased holding capacity within patient tissue.

42. The system of claim 35 wherein the aperture within the stem includes an alignment structure to facilitate proper alignment and insertion of the tool through the aperture within the stem.

43. The system of claim 35 further including an alignment member for facilitating proper alignment and insertion of a tool for controlling the retractable barb, the alignment member being coupled to the implantable medical device.

\* \* \* \* \*